US011458243B2

(12) United States Patent
Stiehl et al.

(10) Patent No.: US 11,458,243 B2
(45) **Date of Patent: *Oct. 4, 2022**

(54) IRRIGATION DEVICE AND SYSTEM FOR DELIVERING PRESSURIZED FLUID TO SAME FOR WOUND LAVAGE AND BIOFILM CONTROL

(71) Applicants: James Bowen Stiehl, Salem, IL (US); Kurt R. Stiehl, Los Gatos, CA (US)

(72) Inventors: James Bowen Stiehl, Salem, IL (US); Kurt R. Stiehl, Los Gatos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/732,102

(22) Filed: Apr. 28, 2022

(65) Prior Publication Data

US 2022/0265916 A1 Aug. 25, 2022

Related U.S. Application Data

(63) Continuation of application No. 16/482,650, filed as application No. PCT/US2018/054737 on Oct. 5, 2018, now Pat. No. 11,351,296.

(Continued)

(51) Int. Cl.
*A61M 1/00* (2006.01)
*A61M 3/02* (2006.01)

(52) U.S. Cl.
CPC .......... *A61M 3/0258* (2013.01); *A61M 3/022* (2014.02); *A61M 3/0216* (2014.02);
(Continued)

(58) Field of Classification Search
CPC ........ A61M 11/006; A61M 2205/3334; A61M 3/0258; A61M 3/0279; A61M 1/882; A61M 1/77; A61M 1/0058; B05B 1/048
See application file for complete search history.

(56) References Cited

U.S. PATENT DOCUMENTS 3,227,158 A 1/1966 Mattingly
3,754,710 A 8/1973 Chimura
(Continued)

FOREIGN PATENT DOCUMENTS

CN 203196051 U 9/2013
IN 865/MUM/2005 4/2006
(Continued)

OTHER PUBLICATIONS

International Search Report and Written Opinion for International Application No. PCT/US2018/054737, dated Mar. 25, 2019, 14 pages.

*Primary Examiner* — Rebecca E Eisenberg
(74) *Attorney, Agent, or Firm* — Foley & Lardner LLP

(57) ABSTRACT

A medical device is provided for irrigation of a patient wound site. The device contains a tube having a proximal portion adapted to receive an irrigation solution, a distal portion having a nozzle and an intermediate portion for transporting the solution. The tube has a barrel portion that may be manipulated by a user to position the device relative to the wound site. A distinctive nozzle has a body formed with a distally leading channel presenting a semispherical first spatial conformation and a proximally leading opening formed in the body presenting a second spatial conformation intersecting the semispherical terminus. This geometry, derived from principles of flow mechanics discussed herein, defines what will be described as an "effective diameter" of the nozzle. An assembly and system utilizing the device am also disclosed. The invention utilizes a fluid-isolating durable peristaltic pump for a continuous flow of irrigation solution, along with a single use tube set that embodies the device.

19 Claims, 16 Drawing Sheets

Related U.S. Application Data

(60) Provisional application No. 62/714,379, filed on Aug. 3, 2018, provisional application No. 62/584,809, filed on Nov. 11, 2017.

(52) U.S. Cl.
CPC ....... *A61M 3/0279* (2013.01); *A61M 2202/04* (2013.01); *A61M 2205/3334* (2013.01); *A61M 2207/10* (2013.01)

(56) References Cited

U.S. PATENT DOCUMENTS

| | | | |
|---|---|---|---|
| 4,963,306 | A | 10/1990 | Weldon |
| 5,178,162 | A | 1/1993 | Dose |
| D334,803 | S | 4/1993 | Discko, Jr. |
| 5,236,426 | A | 8/1993 | Schottes et al. |
| D357,065 | S | 4/1995 | Castellini |
| 5,419,772 | A | 5/1995 | Teitz et al. |
| D359,119 | S | 6/1995 | Dragan et al. |
| 5,460,490 | A | 10/1995 | Carr et al. |
| 5,624,419 | A | 4/1997 | Ersek et al. |
| 5,848,998 | A | 12/1998 | Marasco, Jr. |
| 6,022,329 | A | 2/2000 | Arnett et al. |
| D438,954 | S | 3/2001 | Orsing |
| D451,597 | S | 12/2001 | Suh |
| 6,830,556 | B2 | 12/2004 | Harmon et al. |
| 7,273,359 | B2 | 9/2007 | Slight et al. |
| D571,458 | S | 6/2008 | Kataoka et al. |
| 7,618,430 | B2 | 11/2009 | Scheib |
| 8,568,375 | B2 | 10/2013 | Marasco |
| 8,636,709 | B2 | 1/2014 | Hirsch |
| D710,495 | S | 8/2014 | Wu et al. |
| 9,039,967 | B2 | 5/2015 | Tennican et al. |
| 9,326,665 | B2 | 5/2016 | Slenker et al. |
| D771,248 | S | 11/2016 | Ruiz et al. |
| D771,819 | S | 11/2016 | Pieroni et al. |
| D774,908 | S | 12/2016 | Eckstein et al. |
| D809,123 | S | 1/2018 | Ishikawa et al. |
| 2007/0069049 | A1 | 3/2007 | Lipthal et al. |
| 2010/0286636 | A1 | 11/2010 | Braendli |
| 2012/0021374 | A1 | 1/2012 | Cacka et al. |
| 2015/0258257 | A1 | 9/2015 | Kidman et al. |
| 2016/0175496 | A1 | 6/2016 | Ahluwalia |
| 2017/0246360 | A1 | 8/2017 | Yamasaki et al. |

FOREIGN PATENT DOCUMENTS

| | | | |
|---|---|---|---|
| WO | WO-86/04247 | A1 | 7/1986 |
| WO | WO-2011/039760 | A1 | 4/2011 |

FIG. 18
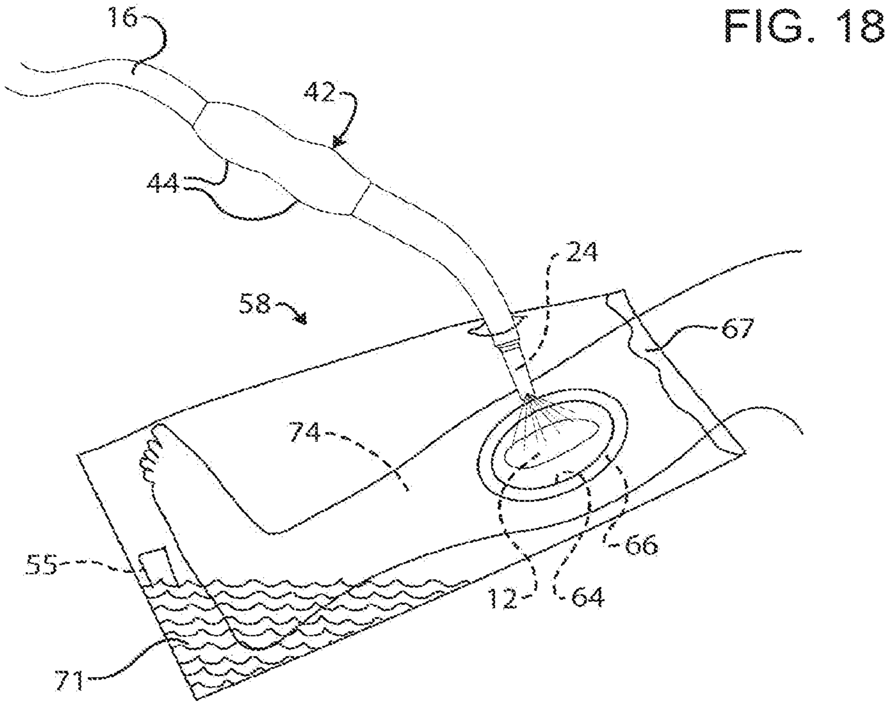
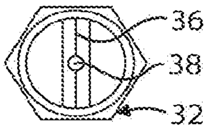
FIG. 20A
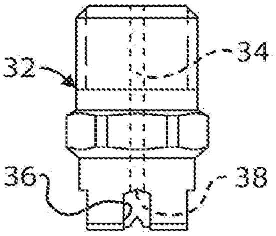
FIG. 19
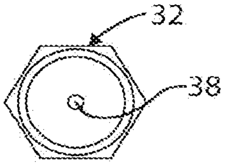
FIG. 20B

IRRIGATION DEVICE AND SYSTEM FOR DELIVERING PRESSURIZED FLUID TO SAME FOR WOUND LAVAGE AND BIOFILM CONTROL

CROSS-REFERENCE TO RELATED APPLICATIONS

This application is a continuation of U.S. application Ser. No. 16/482,650, filed Jul. 31, 2019, which is a 371 U.S. national application of International Application No. PCT/US2018/054737, filed Oct. 5, 2018, which claims the benefit of and priority to U.S. Provisional Application No. 62/584,809, filed Nov. 11, 2017, and U.S. Provisional Application No. 62/714,379, filed Aug. 3, 2018, all of which are incorporated by reference herein in their entireties.

TECHNICAL FIELD

The current invention relates generally to irrigation devices for patient wound lavage, and to systems utilizing such devices for delivering pressurized irrigation solution to the wound site, particularly for outpatient settings where suction is not required or is not readily available.

BACKGROUND

Wound irrigation is considered a salient feature of clinical management in treating chronic open wounds, decubiti, vascular ulcers, and wound breakdown. The critical elements of the method are delivery, volume of fluid, and solution additives. Delivery can include powered/mechanical pumps, pressure canisters, thumb operated bulb syringes, piston syringes, plastic bottles that are hand squeezed for spray from a nozzle, and simply pouring fluid from a kidney basin. An important consideration is the aerosolized particles that can result from the splatter effect of high flow and pulsatile irrigation systems. This can expose the patient and healthcare professionals to air-born contaminants. Documented studies have shown that 45% of the skin and mucous membrane seeding occurs to the eyes usually resulting from inadequate use of federally mandated eye protection. Contamination of the eye conjunctiva has been well documented with HIV virus and Hepatitis C infections from the splash effect.

The optimal pressure and rate of fluid flow remains controversial as high flow is considered important to dislodge bacteria and the biomass film created by the bacteria. High pressure is considered to range from 15 to 35 PSI. While this level of force is considered adequate to remove bacteria, soft tissue damage, impaired immune response, and forcing debris deeper into the wound are hazards. Experts have concluded that 8 to 12 PSI of fluid pressure is adequate to dislodge bacteria eliminating the other effects. Studies comparing the efficacy of pulsatile lavage versus other flow types are inconclusive, but one study showed pulsatile flow was clearly less effective compared with at least one other type of flow (elucidated with respect to the invention described herein) in clearing Staph. aureus in infected rabbit wounds. The optimal volume of fluid irrigation is also inconclusive but lavage of up to 10 liters of fluid in large open wounds has been recommended.

Additives have included a variety of antiseptics including hydrogen peroxide, chlorhexidine gluconate (CHG), sodium hypochlorite, and parachloroxylenol but FDA clearance has been limited by lack of conclusive benefit and the possible toxicity to local host cells when higher concentrations are used. Cell and tissue culture studies with povidone-iodine and sodium hypochlorite have shown that they can be diluted sufficiently to mitigate the tissue toxicity effects without eliminating their bactericidal activity; however, these diluted concentrations were significantly lower than is typically used in clinical practice. Similar dilutional studies with hydrogen peroxide and acetic acid have shown that they lose their bactericidal activity before they lose their tissue toxicity. It is notable that the only antiseptic currently with FDA clearance for debriding and cleansing wounds is an irrigation fluid containing sterile water and 0.05% CHG in a medical device. A recent study of the use of 0.05% CHG with sterile water as an irrigation solution against selective gram-positive and gram negative surgical isolates, including methicillin-resistant *Staphylococcus aureus*, revealed a 5- to 6-log reduction in bacteria recovery at 1 and 5 minutes. Additionally, significant reductions (P values ranging from $<0.05$ to $<0.01$) in bacterial recovery from the surface of 4 different biomedical devices were seen when exposed to the same irrigation solution. Irrigation with this combination prior to wound closure could have a significant impact on the risk of surgical site infections.

In surgical wound debridement, a prominent industry has developed around the use of a mini-piston pump that is battery operated and can be delivered to the surgical field with a sterile and disposable hand held apparatus. The pump is a simple volume displacement device that has one piston cylinder, resulting in a variable pressure throughout the pump cycle. Pressure is reduced by the suction cycle of fluid inflow. This characteristic drives a cyclic pulsatile flow of fluid that has been advocated to debride the wound and remove foreign biomass produced by bacteria.

An important consideration is to understand the physics of fluid mechanics by which these pulsatile systems operate. The battery powered mini-piston pump functions much as any piston system where there is a drive shaft, in this case driven by a small electrical motor powered by a battery pack. The piston system passively draws in fluid from the reservoir system and then drives this fluid downstream into the pump channel that delivers the fluid to the wound. For this system, the pump is powered to create a maximum displacement force that can be measured in pounds per square inch. This has been established by FDA guidelines to have a ceiling of 15 PSI. Therefore, whatever the speed of the pump or revolutions per minute, the pump pressure remains fixed by the force of displacement of the piston. The variables of performance can be altered by the flow rate determined by the revolutions of the pump and the velocity of flow. Flow velocity is determined by the inner dimensional area of the tube which the fluid passes to exit at the pump tip and be sprayed onto the wound.

The other factor to consider is the splatter effect magnified by the pulsatile flow. Again, the pressure of the piston pump is constant causing the same splatter effect even at lower RPMs. The pulsatile flow effect is minimally seen in the peristaltic pumps at lower RPMs and disappears at higher RPM's. As fluid is incompressible, the pressure drops very slightly with the wave drawing fluid behind the fluid roller. This allows for a steady continuous stream flow of fluid from the tip which some believe is more effective at removing biomass compared to the pulsed stream. To reiterate, the pump pressure remains the same at the high and low speeds that the piston pump operates, but the amount of fluid that the pump moves changes as a function of pump speed or revolutions per minute. In actual practice, there may be a limit to the amount of piston RPM's possible.

The pulsatile irrigation systems are single use because the pump, tubing and handle come into contact with the operating field adjacent the wound site, which thereby renders these elements non-sterile. This happens dramatically in surgery, where a combined suction-irrigation instrument is relied upon to siphon-off spent irrigation solution while allowing continued free access to the surgical site, yet there remains considerable splattering of operating room personnel (of whom most wear head gear with face shields), because the surgical wound site is not enclosed. Even where a shielding enclosure is employed post-operatively on an outpatient basis, the irrigation instrument becomes contaminated within the operating field defined by the enclosure, thus it must be discarded after a single use. The piston pump is in fluid communication with the instrument and exposed to spent irrigation solution during the procedure and this must also be thrown away, whether or not the pump is within or adjacent the irrigation instrument. In fact, pulsatile irrigation-suction guns have been used in combination with enclosure bags on outpatient procedures, as will be explained in the section immediately below, although the suction feature is often disabled by cutting off the hose leading into the pulsatile gun. Moreover, the predominant pulsatile gun models on the market are actuated by a finger trigger that controls the pump pressurizing fluid in the gun.

Some have sought to contain the backsplash emanating from the wound site being irrigated, by providing barriers, e.g., transparent bags, which surround the operating field. However, these barriers remain complicated, expensive and/or inadequate in the main, as well as the systems where used. These still leave problems of pulsatile irrigation unresolved.

PRIOR ART

U.S. Pat. No. 5,624,419 to Ersek, et al., entitled "Closeable, Disposable Wound Care System", discloses a clear receptacle having an adhesive portion for sealing to the patient. The receptacle is a bag for retaining fluids along with a spraying or irrigation member such as a syringe. This enables the wound irrigation procedure to be carried out in a closed system. Upon completion, the receptacle may be completely sealed and disposed of as appropriate to avoid cross-contamination of caregivers.

U.S. Pat. No. 5,178,162 to Bose, entitled "Splash and Spill Resistant Extremity Irrigation and Debridement Surgical Drape", seeks to isolate an injured limb creating a self-enclosed system through which irrigation and debridement is performed. The drape isolates the injured limb from the remainder of the body as well as the surgical team in order to create a fluid splash barrier to prevent the splash or spill of contaminated blood or surgical irrigation solutions. Perforated fenestrations provide access for hands of the operator and instruments used.

U.S. Pat. No. 8,636,709 to Hirsch, entitled "Fluid Containment Apparatus", shows a dual-horned upper containment structure wherein pressurized irrigation fluid is supplied to a (homed) inlet and suction supplied to an (homed) outlet, between which fluid circulates within an open lower face of the containment structure and an articulating ring situated atop a bandage that has a cut-out for a wound site (denoted by segments A, B and C). This containment assembly is said to enable pulse lavage irrigation of wounds in a non-controlled setting while providing containment of contaminated irrigation fluid, said to prevent exposure of individuals and surfaces in proximity to the patient to infectious materials.

U.S. Pat. No. 5,848,998 to Marasco, Jr., entitled "Tissue Debriding Apparatus", along with its progeny patents/applications, commonly describe an approach involving plastic enclosure bags used with pulsatile irrigation guns, which is promoted by PulseCare Medical LLC of North Andover, Mass. ("PulseCare") as Continuous Pulsatile Irrigation ("CPI"). The plastic CPI bag used provides fluid effluent collection and is directed to fostering a dry operating field by creating an arrangement of connected bags. The wound irrigation bag allows for a tent like closed system that keeps the patient and the air, dry from the irrigation process. One or more ports are located so that the proximal side edge may be removed allowing for a pulsatile irrigation gun to be inserted for the irrigation. The caregiver then irrigates 3 liters of saline onto the open wound, irrigating, debriding and hydrating the wound surface. The force of the pulsatile irrigator is set at slightly below 15 PSI, considered by the United States Food and Drug Administration (FDA) as a safe irrigation force that will not damage wound granulation tissue.

The PulseCare CPI system uses two different bags with a channel that extends from an irrigation bag to a collection reservoir. The plastic thickness is 2.0 MIL for the wound bag and 2.5 MIL for the reservoir bag, which appears adequate for the system. In use, the bags are placed in such a way that gravity drives the effluent from the irrigation bag into the collection bag where flocculating granules are provided that are activated to solidify 3 L of saline, the collection bag is then folded over and disposed of in the trash or other prescribed medical waste container. This can be done as a biocide is included that kills all biologicals in the irrigated fluid. The system is said to, in some cases, be considered not a "red bag" biological for disposal in any trash dump.

Negative issues include the unit cost of the PulseCare CPI bag, which can retail for $32 (USD) at present and is further supplied non-sterile, and the fact that the CPI bag system requires a custom multi-step manufacturing process, which the instant invention proposes to simplify and improve. The bag requires sealing of all the edges by hand. Then there is placement of the irrigation channels that require double seals to create an open channel. The collection reservoir also requires a double seal for a total of 8 double seals. There further remain additional steps of folding and packaging the bags.

It is known in the prior art that the use of a pulsating stream of fluid, such as water, can be utilized to cleanse body tissue of contaminants. U.S. Pat. No. 3,227,158 to Mattingly, entitled "Method and Apparatus for Oral Hygiene", describes a system that creates a fluid jet lavage stream that could cleanse the surgical site. The invention utilizes a piston pump, creating a pulsatile flow measured by stroboscope with a frequency of approximately 1150 cycles per min, the stroke of the piston being 7/16 inch and the orifice. 0.038 inch in diameter, with a full pressure curve starting at zero pressure and peaking at approximately 90 pounds per square inch ("PSI"). This discharge pressure may be carefully controlled by adjusting a bypass channel on the discharge side of the pump down to a level of 10 PSI. The wave form of the jet lavage at the beginning of the exhaust stroke of the pump elevates steeply, indicating that there is a shock characteristic. This device was designed for the oral cleaning of teeth, with patients experiencing definite gum pain at higher level of force application.

U.S. Pat. No. 6,022,329 to Arnett et al., entitled "Irrigation Handpiece with Built in Pulsing Pump", describes pulsatile irrigation by a mini-piston pump with a battery-powered motor that is housed in a hand-piece that has been sterilized for use in the operative surgical field. This device is self-contained, does not require any connections to a power source or compressed air, and only requires the external connection of the irrigation liquid source. While advocates of pulsed irrigation believe the impact of the liquid droplets have an advantage to dislodge bacteria, disrupt biomass, and remove debris, there is concern of the potential splatter effect and aerosolizing particles that expose the patient and healthcare professionals to air-born contaminants. Documented studies have shown that 45% of the skin and mucous membrane seeding occurs to the eyes, usually resulting from inadequate use of federally mandated eye protection. Contamination of the eye conjunctiva has been well documented with HIV virus and Hepatitis C infections resulting from the splash effect.

U.S. Pat. No. 6,830,556 to Harmon et al., entitled "Debridement Extension Providing Irrigation and Mechanical Scrubbing for Removal of Dead, Devitalized, or Contaminated Tissue from a Wound", describes a long gun extension for treating deep tract wounds, such as in orthopedic surgical procedures. The manually actuated gun with tip extension mechanically debrides the wound tissues to be removed, the extension having suction and irrigation ports supplied through a manually actuated gun with pump that pressurizes the irrigation fluid.

U.S. Pat. No. 9,326,665 to Slenker et al. entitled "Surgical Instrument, System, and Method for Biofilm Removal", is adapted to dispense pressurized irrigant from an irrigation duct in the instrument through a tip toward a layer of bacterial biofilm. The instrument has an elongated introducer that may be shaped to correspond to the contours of a patient's nasopharyngeal passages and cavities. A controller regulates flow of suction and irrigation to and from the instrument, and may alternatively be operated by a foot pedal by the user of the system. Multiple bags may infuse different fluids which are drawn into the supply tube where a pump situated in a gun pressurizes the fluid and delivers same to a gun actuated manually by a trigger. The instrument functions as an endoscope to visualize accumulations of biofilm, then delivers irrigation fluid under pressure to the biofilm site and aspirates the loosened biofilm through a suction cannula for removal by the instrument.

Two competing suction-lavage products have been designed for use in orthopedic surgery. One branded instrument is the PulsaVac®, manufactured and sold by Zimmer, Inc.® of Warsaw, Ind. The other brand, also well-known, is the Interpulse® manufactured and sold by Stryker Instruments® of Kalamazoo, Mich. Both have enjoyed considerable success over the years.

An alternative irrigation delivery, and a subject of this invention, can be accomplished by the use of a peristaltic pump. The pump is non-sterile and is placed at some distance from the surgical field. However, the tube-set through which irrigation solution passes to the surgical field, is a "closed" sterile system. Two or more rollers advance the fluid by squeezing the tubing against a circumferential rim that contains a segment of the tubing. There may be some form of uncharacteristically uneven flow at low RPMs of the peristaltic pump but at typical RPMs, the flow is virtually direct and continuous.

Historically, the peristaltic pump was patented by Eugene Allen in 1881 and popularized by Dr. Michael DeBakey in 1932 when Dr. DeBakey designed a peristaltic pump eventually to be used as a heart-lung machine in cardiac bypass surgery. U.S. Pat. No. 7,273,359 to Blight et al., entitled "Peristaltic Irrigation Pump System", is representative of an irrigation and distension pump system for surgical use. Numerous system designs are said to be known by which the tubing used with the pumps may be configured into surgical tube sets adapted for various applications (arthroscopy, laparoscopy, irrigation, etc.). The tube sets may be coded to identify the procedure for which they are designed and can be relatively easily engaged with the pump and other components. These designs may generally utilize a cassette in the form of a molded housing which retains a portion of the tubing so that the engagement of the tubing with the peristaltic pump simply requires the attachment of the cassette adjacent the peristaltic pump roller assembly rather than the laborious process of threading a tube around the roller assembly and securing it in place.

While there are many applications to these peristaltic pumps, study of the fluid mechanics reveal that certain parameters can be optimized for use in clinical practice. The use of peristaltic pumps in wound debridement is not well-elucidated concerning how these systems function. That is, pump head pressure, flow rate, and flow velocity have not been categorized for clinical efficacy and safety. The important difference from a piston pump is the fact that the peristaltic pump flow rate is constant and the pressure is determined by the RPM's. This control determines the force generated by the system. As the pump RPM's increase, the flow rate increases, and the pressure of the system increases. As compared to the piston pump, where the pressure becomes the variable while flow remains constant for a given RPM. As understood by practice of the present invention, with the Bernoulli Effect, the inner tube dimensional area determines the velocity at the tip. This function has value if there is a reason to deliver different fluids at differing flow rates. This discussion will be continued below, in conjunction with the choice of parameters taught by the practice of the subject invention.

The afore-mentioned approaches of others generally have not transcended the problems inherent in conventionally-used pulsatile irrigation methods, nor have these sought to employ peristaltic pumps.

The afore-mentioned approaches of others, using pulsatile pumps, insufficiently address the provision of a continuous flow of an irrigation solution to an irrigation instrument, and the opportunities for improvement using other means of wound irrigation, apart from pulsatile pumps.

These approaches of others have not reduced splatter by the pulsatile delivery system, in the operating field.

The approaches of others in attempting to contain the pulsatile irrigation splatter by means of enclosing the wound site have not resulted in a simple, economical and effective containment, during the delivery of wound irrigation solution.

There is a need for a continuous, peristaltic irrigation device and a system for outpatient wound debridement, irrigation and removal of biofilm.

SUMMARY OF INVENTION AND ADVANTAGES

According to an aspect of the present invention, a medical device is provided for irrigation of a patient wound site. The device contains a tube having a proximal portion adapted to receive an irrigation solution, a distal portion having a nozzle and an intermediate portion for transporting the solution. The tube has a barrel portion that may be manipulated by a user to position the device relative to the wound site. A distinctive nozzle has a body formed with a distally leading channel presenting a semispherical first spatial conformation and a proximally leading opening formed in the body presenting a second spatial conformation intersecting the semispherical terminus. This geometry, as will be derived from principles of flow mechanics discussed below, defines what will be described as an "effective diameter" of the nozzle.

It is this numerical value, i.e., range of values, which determines a corresponding spray pattern and other flow characteristics, from the nozzle onto the wound. Several preferred embodiments of the above device will now be described, in relation to assembling of various arrangements of its features. The nozzle is also preferably in a fixed position on a distal tip of the tube, which is also preferably captured within a hand piece that simultaneously prevents rotation of the tube relative to the hand piece, more preferably the hand piece is affixed to the barrel of the tube, preventing relative motion therebetween. The device may preferably have a hand piece formed with an integral finger grip affixed to the barrel of the tube, preventing relative motion therebetween. Alternatively, the hand piece is plastic and elongated with a bulbous molded shape, capturing the tube and nozzle at a distal tip of the tube, preventing relative motion therebetween. It is also preferred that the hand piece structurally captures the nozzle at a distal tip of the tube, including complementary anti-rotation structures preventing relative motion therebetween. Alternatively, the hand piece captures the nozzle at the distal tip of the tube, the nozzle being made of plastic and bonded to the tip and hand piece by an adhesive or by sonic welding, preventing relative motion therebetween. The nozzle may alternatively be a metallic material such as brass or stainless steel and mechanically fastened to the hand piece at the distal tip, using a threaded or crimped connection that aligns the nozzle channel with the internal diameter of the distal tip. A vent hole is formed in the hand piece and tube, to allow manual regulation of the flow of irrigation solution by a user of the device.

Various preferred configurations of the nozzle will now be described. The device preferably includes a nozzle having its proximally leading opening formed with a spatial geometry selected from a wedge, a cone, a tetrahedron or a star shape formation in the body. The nozzle more preferably has a proximally leading generally wedge shaped formation in the body of the nozzle and presents an apical spatial portion that intersects with the semispherical terminus of the channel. It is alternatively preferred that the nozzle has a proximally leading generally conically shaped formation in the body of the nozzle, the cone presenting an apical spatial conformation that intersects with the semispherical terminus of the channel. The nozzle may be made of an injection-molded plastic material such as PVC or the like, depending on cost and design for moldability, whereas the tube is made of an extruded plastic material, also possibly PVC. The tube may extruded with a polygonal cross-section and the hand piece and nozzle injection molded with complementary polygonal cross-sections, respectively, which prevents relative motion therebetween.

Various preferred performance attributes will now be discussed. The preferred spray pattern, determined by the effective diameter of the nozzle, is a flattened pattern generally approaching perpendicularity to the axis of the channel, which corresponds to the profile and proportions of typical wounds. The angle of incidence of the generally flat spray pattern relative to the channel axis is greater than zero but less than about 30 degrees. Alternatively, an angle of incidence of the spray pattern relative to the channel axis, as determined by the effective diameter, may be generally arrow-shaped greater than about 60 degrees and less than about 90 degrees. Alternatively, the shape and angle of incidence of the spray pattern relative to the channel axis, as determined by the effective diameter of the nozzle, may generally be conical and between about 30 degrees and about 60 degrees.

According to another aspect of the present invention, a wound irrigation assembly includes a device with an extruded plastic tube having a proximal inlet for connection with a source of irrigation solution and a distal tip with an outlet. A hand piece captures a barrel of the tube. A nozzle is aligned with the inner diameter of the tube outlet and is captured by the hand piece, preventing relative motion therebetween. A plastic containment and collection bag having a generally tubular construction includes a lower patient-side layer and an upper device receiving layer. The patient-side layer has a fenestration sized to accommodate a wound and a dual sided adhesive tape with one side adhered on the patient side layer along an outer border of the fenestration. The tape forms a lateral flow barrier when the opposite side of the tape is adhered to a patient's body in alignment with the wound. An upper side of the bag has a random access point that may be chosen by the user to make a small cut in the bag through which the device nozzle passes into a sterile operating field within the bag. The nozzle has a body formed with a distally leading channel presenting a semispherical first spatial conformation and a proximally leading opening formed in the body presenting a second spatial conformation intersecting the semispherical terminus. This relationship defines an effective diameter of the nozzle that determines a corresponding spray pattern from the nozzle onto the wound.

The bag of the assembly preferably contains a biocidal flocculent material that solidifies effluent within the bag for easier collection and disposal. The bag of the assembly preferably defines a rectangular shape, being sealed at the creases on the opposed longitudinal sides (i.e., in the spooling direction) and cut and impact-sealed at the ends of the bag blank. This configuration ideally accommodate a torso wound irrigation procedure, the fenestration being formed intermediate the longitudinal sides and ends of the bag to be adhered by the tape dam to the patient's body. Alternatively, the bag is cut and sealed on only one of the ends so that three sides are closed. There is thus an opening at the one end to allow ingress of an upper or lower bodily extremity for irrigation of a wound thereon. The open side is secured by tape or gathers around the extremity to prevent disengagement of the bag prior to completion of the procedure. The tape dam constrains lateral flow of effluent within the bag for collection and disposal, similar to the torso bag design. The nozzle of the assembly has an alternately preferred proximally leading generally wedge shaped formation in the body of the nozzle and presents an apical spatial portion that intersects with the semispherical terminus of the channel to determine the spray pattern. Alternatively the assembly nozzle has a proximally leading generally conically shaped formation in the body of the nozzle, the cone presenting an apical spatial conformation that intersects with the semispherical terminus of the channel. The assembly nozzle preferably has an effective diameter that determines a generally flat spray pattern coinciding with a contour of the wound.

A system for irrigation of an outpatient wound will now be described. There is a device including a tube having an inlet and outlet with a barrel portion therebetween and an elongated hand piece mounted in fixed position around the barrel. A nozzle is mounted at a distal portion of the tube and hand piece without relative motion between nozzle, tube and hand piece. A generally rectangular clear plastic tubular containment and collection bag having at least three and up to all four sides of the bag periphery is cut and sealed as described above relative to the assembly. A fenestration is formed in the lower patient side of the bag bordered by a dual-sided tape dam which, when adhered also to the patient, confines lateral flow of effluent to the space within the bag for collection of the effluent and disposal of the bag. The fenestration and corresponding tape dam periphery are selected from generally rounded or polygonal shapes, depending upon a given wound site.

The system preferably includes a sterile packet with a disposable wipe containing an antiseptic such as Chlorhexidine Gluconate or the like in terms of safety and efficacy. Another alternative antiseptic is Hypochlorous Acid that has shown effective bacterial biofilm treatment, however, the regulatory approval of this antiseptic remains in progress relative to wound irrigation operations.

Importantly, the device, assembly and system described above further utilize a peristaltic pump connected to a source of irrigation solution and to an inlet of the tube, respectively. The pump delivers a flow rate between about 800 milliliters per minute to about 2550 milliliters per minute at a constant pressure of 15 PSI, wherein the effective diameter of the nozzle is between about 1.1 millimeters and 1.93 millimeters, and further wherein an effective diameter of 2.14 millimeters creates a distal tip flow pressure of 10 PSI for an optimal flow rate of 2550 milliliters per minute. This results in a three liter sack of irrigation solution being drained in merely a few minutes.

An advantage of the present invention is that a completely sterile device enters the sterile surgical field. A fluid-isolating peristaltic pump operated by a foot pedal of the invention remotely transports a sterile irrigation solution that remain from outside the sterile operating field into the wound site where only the tubing of the pump and effluent are disposed of after a single use.

Another advantage of the present invention is a pump that can quickly and smoothly deliver a continuous flow of irrigation solution in an optimal, i.e., flat spray onto the wound site, without aerosolized biofilm spattering as experienced with hand actuated guns driven by pulsatile pumps that must be disposed of after a single use.

Yet another advantage of the present invention is an inexpensive tube set that is driven by a durable pump and foot pedal control shown to be reusable for a lengthy life cycle with a multitude of reliable operations.

Still another advantage of the present invention is a biofilm removal in the effluent generated by the procedure, according to the invention, rather than entrained biofilm arising from the wound site into the air.

The features and advantages of the disclosure will be set forth in the description which follows, and in part will be apparent from the description, or may be learned by practice of the disclosure without undue experimentation. The features and advantages of the disclosure may be realized and obtained by means of the devices and combinations particularly pointed out in the appended claims.

BRIEF DESCRIPTION OF THE DRAWINGS

FIG. 9 is a top plan view of the extremity bag (FIGS. 4-8) showing one of its opposed ends sealed and cut with the other end unsealed with double-sided tape and/or other closure along the open, unsealed margin of the bag and the tape dam surrounding the fenestration having a preferred ovoid shape as previously mentioned, according to the present invention;

FIG. 18 is a side elevational view of an extremity bag in place on a patient, showing the inventive device entering the sterile field of the present system, further depicting the flat spray pattern of the device onto a wound surrounded by an oval tape dam and radially spaced fenestration;

FIG. 19 is a side elevational view of the nozzle of FIGS. 17A-B, showing the channel (in phantom) and V-notch, according to the invention;

FIG. 20A is a bottom view of FIG. 19, according to the invention;

FIG. 20B is a top view of FIG. 19, according to the invention;

DETAILED DESCRIPTION OF THE FIGURES

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word “exemplary” is used herein to mean “serving as an example, instance, or illustration.” Any embodiment described herein as “exemplary” is not necessarily to be construed as preferred or advantageous over other embodiments. Likewise, any of the terms “embodiments of the invention”, “embodiment” or “invention” does not require that all embodiments of the invention include the discussed feature, advantage or mode of operation.

Embodiments can be designed as taught herein, to cooperate with nearly any elements that make use of a peristaltic pump and tube set for wound irrigation. For examples, embodiments can be designed to cooperate with various styles and shapes of the present device, assembly and system as will be appreciated by those having ordinary skill in the art.

Nevertheless, for illustrative purpose and in a non-limiting fashion, at least one exemplary embodiment is described herein in reference to the device nozzle. At least another embodiment that is an alternative to the immediately preceding device nozzle is provided. Yet another alternative embodiment thereto is further provided.

Figure 4:
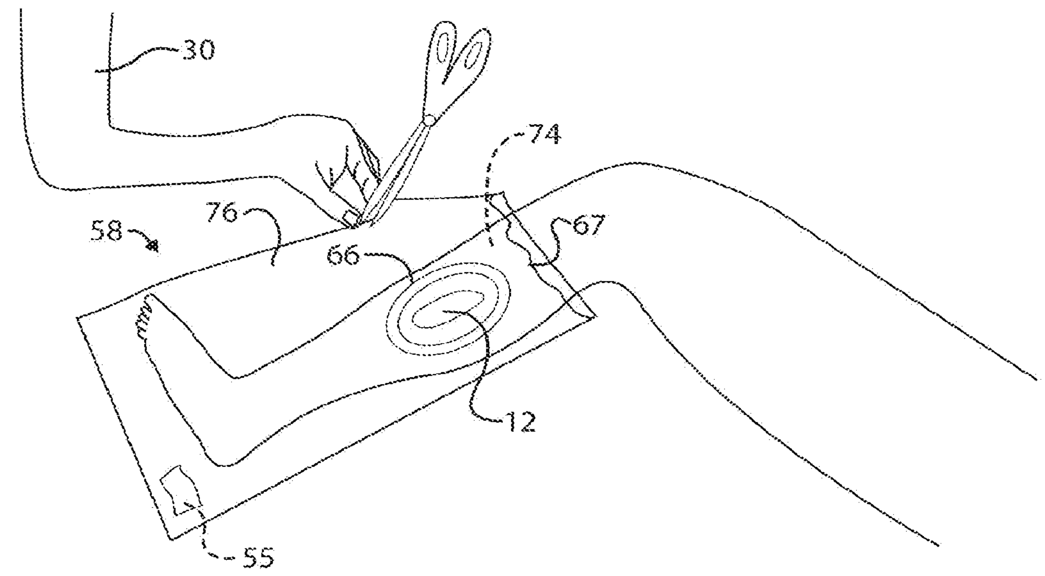
FIG. 4 is a side elevational view of the extremity bag (FIGS. 9-10) being prepared in position with the patient-side of the bag against the patient's inclined lower leg, while a slit is cut by the user into the upper side of the bag (e.g., with scissors) through which the user may then access and treat the wound site preferably after swabbing it with pre-packaged chlorhexidine gluconate antiseptic wipes (e.g., "Irrisept") to kill biofilm, also preferably putting in the closed end of the bag a flocculent biocide material (e.g., Zappatec) that solidifies the effluent (FIG. 5) collected for later disposal, prior to securement of the bag firmly in place, preparing the wound for deployment of a device within the bag to treat the wound with an irrigation solution, on an outpatient basis without requiring a controlled operating setting, i.e., with suction equipment, according to the present invention.
Figure 5:
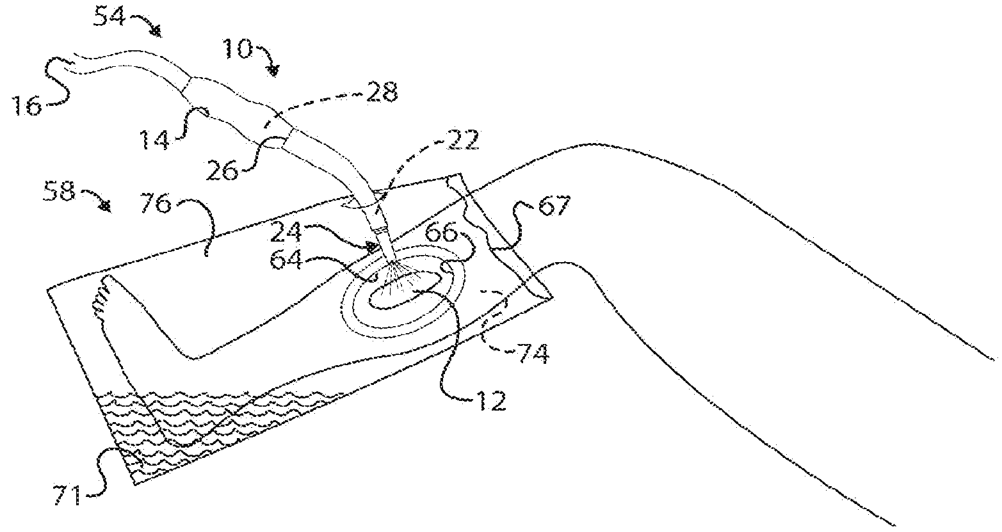
FIG. 5 is a side elevational view of FIG. 4, sequentially depicting the bag securely held around the lower leg defining a sterile field in which a preferred elongated irrigation device (FIGS. 21-32) according to the invention is introduced by the user (not shown) through the slit in FIG. 4, the terminal outlet of the device having a preferred nozzle structure (FIGS. 15-20 and 29) that sprays an irrigation solution in a selected pattern onto the wound site exposed through the fenestration and constrained by the preferred ovoid dam, the effluent flowing away from the wound site and into a non-sterile collection zone such that there is no need for surgical suction to evacuate the effluent allowing treatment on an outpatient basis without a controlled setting, according to the present invention.
Figure 6:
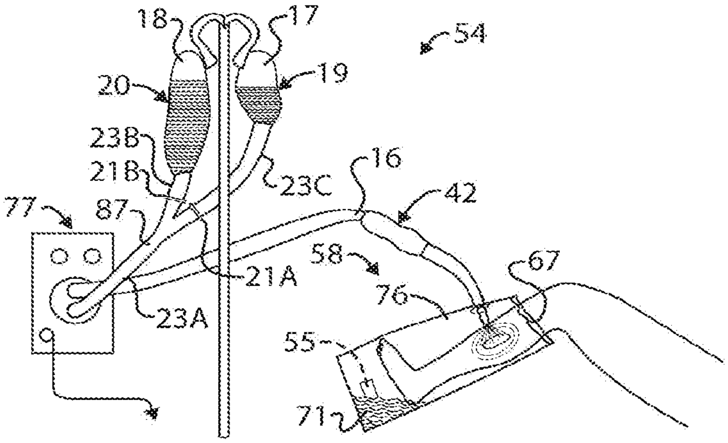
FIG. 6 is a side elevational view of a preferred wound irrigation system employing the inventive device referred to in conjunction with FIG. 5 protruding into the sterile field, further including a fluid isolating roller pump (also known as a peristaltic pump) to which a flexible tube passes from a spiked hanging container thence threaded among the rollers of the pump outside the sterile field to the preferred elongated irrigation device terminating with its nozzle inside the sterile field, the tube conveying a preferably sterile irrigation solution (e.g., saline) from the hanging container to the pump where the solution is pressurized inside the tube to the preferred irrigation device and sprayed through its nozzle in a distinctive pattern onto the wound site, thereby avoiding any direct contact of the solution outside the tube with the pump structures as the solution flows from its sterile source through a non-sterile setting thence into the sterile field as the solution exits the nozzle while remaining sterile with the bag shielding the user (not shown) from aerosolized biofilm and containing the biofilm within the non-sterile spent solution being solidified in the collection zone of the bag, according to the present invention.
Figure 7:
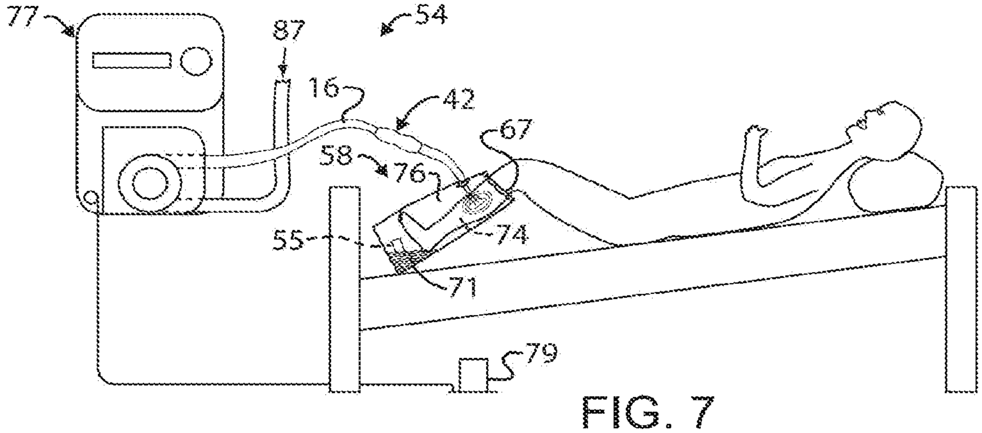
FIG. 7 is a side elevational view of FIG. 6, partially enlarged to more closely show the peristaltic pump and tube set and extended to encompass the inclined patient, further revealing a preferred foot control pedal being electrically connected to the pump (FIGS. 13-14A-14B) for operational control of its speed (RPM) by the user (not shown) of the system of the present invention.
Figure 8:
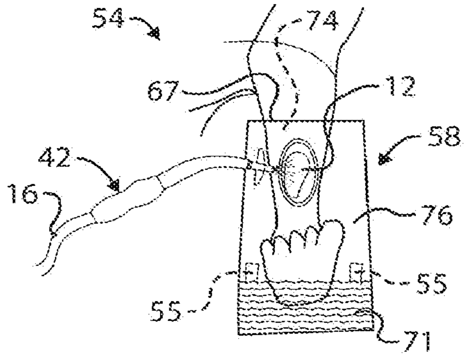

According to one aspect of the present invention, there is generally shown in FIGS. 5-12 and FIGS. 15-32, a medical device 10, for debridement and irrigation of a patient wound site 12. Device 10 contains a tube 14 having a proximal portion 16 adapted to receive an irrigation solution 18 from a reservoir generally indicated at 20, a distal portion 22 of tube 14 having a distinctive nozzle 24 and an intermediate portion 26 for transporting the solution. Tube 14 has a barrel 28 that may be manipulated by a user 30 (shown snipping open an entry slit for the device in FIG. 4) to position device 10 relative to wound site 12. Nozzle 24 has a body 32 formed with a distally leading channel 34 presenting a semispherical first spatial conformation 36 and a proximally leading opening formed in the body presenting a second spatial conformation 38 intersecting the semispherical terminus 36 at a V-notch 40 (FIG. 29). This geometry, as will be derived from principles of flow mechanics discussed below, defines what will be described as an “effective diameter” of the nozzle. It is this numerical value, i.e., range of values, which determines a corresponding spray pattern and other flow characteristics, from nozzle 24 onto wound 12.

Several preferred embodiments of device 10 will now be described, in relation to assembling of various arrangements of its features. Nozzle 24 is also preferably in a fixed position on a distal tip or portion 22 of tube 14, which is also preferably captured within a hand piece generally shown at 42 in its alternative forms (FIGS. 5-8 and 15) that simultaneously prevents rotation of tube 14 relative to the hand piece, more preferably the hand piece is affixed to barrel 28, preventing relative motion therebetween. Device 10 may preferably have a hand piece 42 formed with an integral finger grip 43 consisting of lateral halves 45 held together by pins or the like 47 (FIG. 15) affixed to barrel 28, preventing relative motion therebetween. Alternatively, hand piece 42 is plastic and elongated with a bulbous molded shape indicated at 44, capturing tube 14 and nozzle 24 at a distal tip 22 of the tube, preventing relative motion therebetween. It is also preferred that hand piece 42 structurally captures nozzle 24 at distal tip 22, including complementary anti-rotation structures (not shown) preventing relative motion therebetween. Alternatively, hand piece 42 captures nozzle 24 at distal tip 22, the nozzle being made of injection molded plastic and alternatively bonded to the tip and hand piece, respectively, by an adhesive or by sonic welding (not shown), preventing relative motion therebetween. Nozzle 24 may alternatively be a metallic material such as brass or stainless steel and mechanically fastened to hand piece 42 at distal tip 22, using a threaded 46 or crimped (not shown) fastener that aligns channel 34 with the internal diameter (Arrows 48) of distal tip 22. A vent hole 50 is formed in hand piece 42 and barrel 28, to allow manual regulation of the flow of irrigation solution 18 by user 30.

Various preferred configurations of nozzle 24 will now be described. Device 10 preferably includes nozzle 24 having its proximally leading opening formed with a spatial geometry selected from a wedge shape as shown, a cone shape (discussed but not shown), a tetrahedron or a star shape (not shown) formation 36 in body 32. Nozzle 24 more preferably has a proximally leading generally wedge shaped formation 36 (FIGS. 17A-B and 19-20A-B. Body 32 presents an apical spatial portion 36 such as V-notch 40 that intersects with the semispherical terminus 38 of channel 34. Although not specifically shown in the Figures, it is alternatively preferred that the nozzle has a proximally leading generally conically shaped formation in the body, the cone presenting an apical spatial conformation that intersects with the semispherical terminus of the channel, similarly to what has been illustrated and discussed with respect to the V-notch of the wedge-shaped embodiment elucidated above. Nozzle 24 may be constructed of an injection-molded plastic material such as PVC or the like, depending on cost and design for moldability, whereas tube 14 is made of an extruded plastic material, also possibly PVC. Although not shown in the Figures, the tube may be extruded with a polygonal cross-section and the hand piece and nozzle injection molded with complementary polygonal cross-sections, respectively, which together in the proper manner would prevent relative motion therebetween.

Various preferred performance attributes will now be discussed. The desired spray pattern, determined by the effective diameter of nozzle 24, is a flattened pattern generally approaching perpendicularity to the axis of channel 34, which corresponds to the profile and proportions of a wound 12 typical of that shown, (FIGS. 5-8, 11, 12, 18). The angle of incidence 52 of the generally flat spray pattern relative to the axis 49 (FIG. 15) of channel 34 (FIG. 29) is preferably greater than zero but less than about 30 degrees. Alternatively, an angle of incidence 52 of the spray pattern relative to the axis of channel 34, as determined by the effective diameter, may be generally arrow-shaped greater than about 60 degrees and less than about 90 degrees. Alternatively preferred, the shape and angle of incidence 52 of the spray pattern relative to the axis of channel 34, as determined by the effective diameter of nozzle 24 may generally be conical and between about 30 degrees and about 60 degrees. The two ranges of more acute angles of incidence are not shown, nor is the conical profile formed in the body, though the same are described below as possible embodiments of the present invention, depending on the performance objectives.

Figure 1:
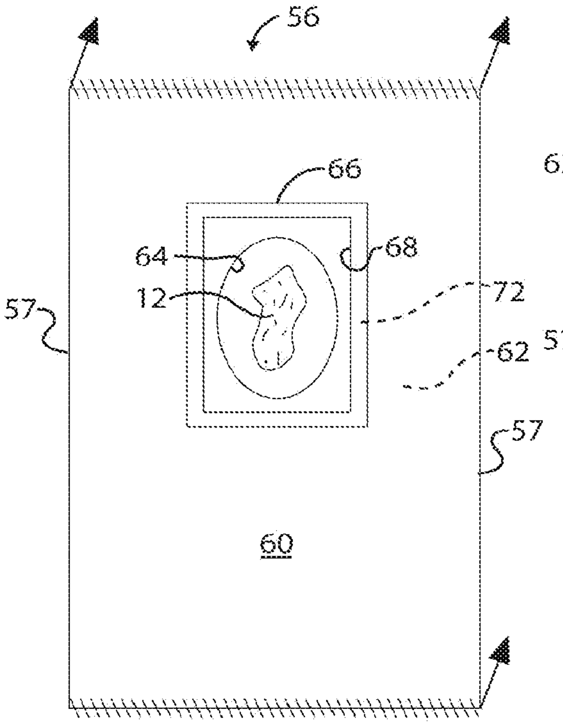
FIG. 1 is a bottom plan view of a torso bag for application onto the patient (arrows) having both ends impact-sealed and cut from spooled clear plastic film tube stock (FIGS. 3A-3B), which bag is utilized by a wound irrigation system of the present invention for shielding a user from biofilm arising during a procedure performed on a patient with an irrigation solution by the system, while collecting effluent during the procedure for disposal afterward, a fenestration being made in the patient-side of the bag to overlay the wound site and a preferred generally polygonal-shaped wound site barrier or dam made of a double-sided tape with a top side adhered to the bag surrounding the fenestration and a bottom side adhered to the patient (FIGS. 9-10), to constrain gravity flow of effluent within the bag.
Figure 2:
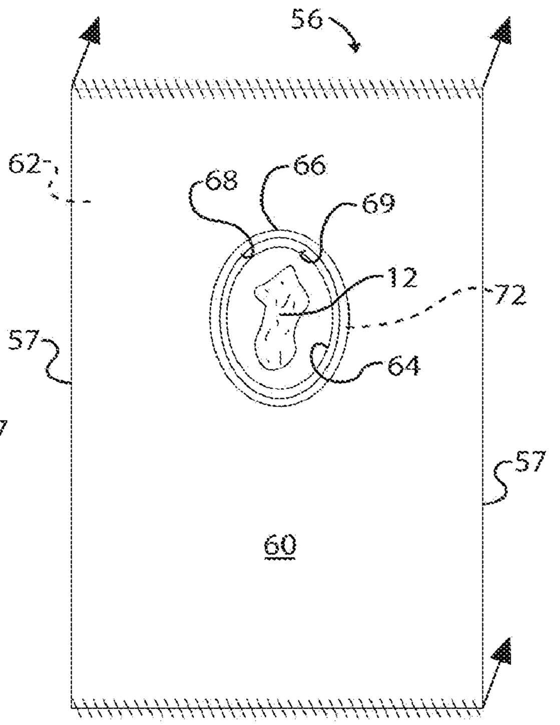
FIG. 2 is a bottom plan view of the bag of FIG. 1, depicting the barrier tape structure of the invention with another preferred, generally contoured shape, such as the ovoid pattern shown.
Figure 3A:
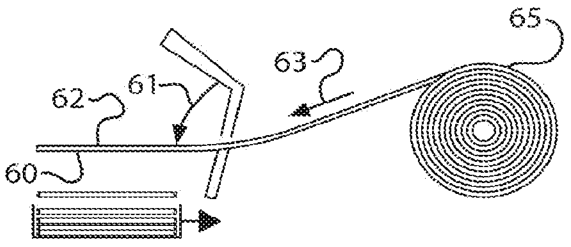
FIG. 3A is a side elevational view of apparatus to make the bags of the present invention, showing a spooled plastic film tube stock being unrolled past an impact sealer that cuts the tube stock to length with or without sealing the ends of the adjacent bags formed by the cut along a common edge or cut zone, which are shown stacked below the apparatus.
Figure 3B:
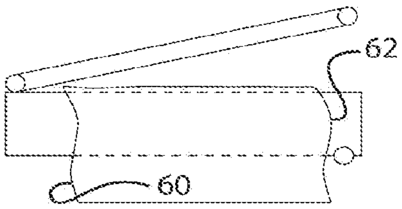
FIG. 3B is a front elevational view of the impact sealer of FIG. 3A, showing a bag being cut to length, either as a bag with one end of the bag being sealed for containment and an opposite end being open and unsealed for passage of a patient's extremity (FIGS. 9-10) and securely gathered at the open end around the extremity by elastic, hook and loop fasteners (Velcro®) and/or double-sided tape, prior to irrigation of the patient's extremity (e.g., lower leg) as in FIGS. 4-8, or alternatively having both ends sealed (FIGS. 1-2) for use in irrigating wounds of a patient's torso (FIGS. 11-12), according to the present invention.
Figure 9:
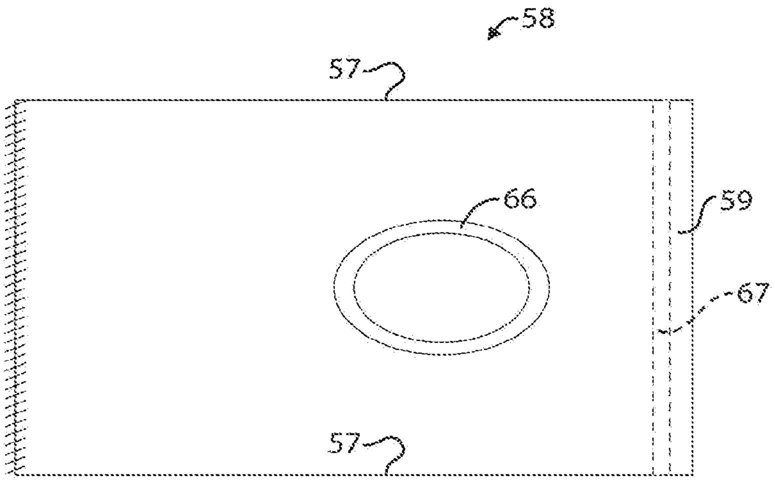
FIG. 9 is a front elevational view of FIGS. 6-7 partially enlarged to show the sterile irrigation solution proceeding from the subject device within the bag (FIGS. 9-10) onto the patient's wound site in the sterile field, according to the present invention.
Figure 10:
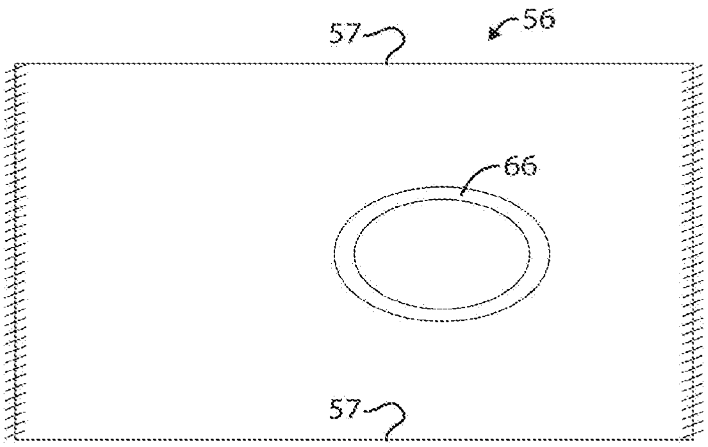
FIG. 10 is a bottom plan view of the bag of FIGS. 1-2, showing the tape having been applied to the patient-side of the bag.
Figure 11:
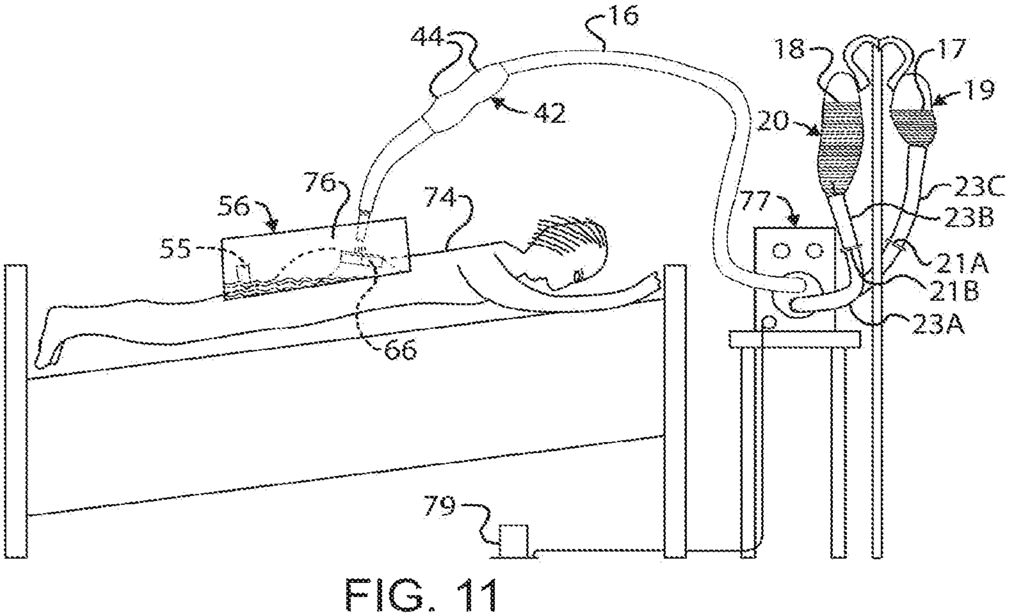
FIG. 11 is a side elevational view of a prone patient, exposing a rear torso wound being treated by the inventive device, particularly an assembly and more particularly in a wound irrigation system (FIGS. 4-8), which is adapted for torso wounds, the system further including the foot pedal-operated peristaltic pump outside the sterile operating field, with tube set transporting the sterile irrigation solution to the sterile field enclosing the wound site, for downstream collection of effluent within the torso bag, according to the present invention.
Figure 12:
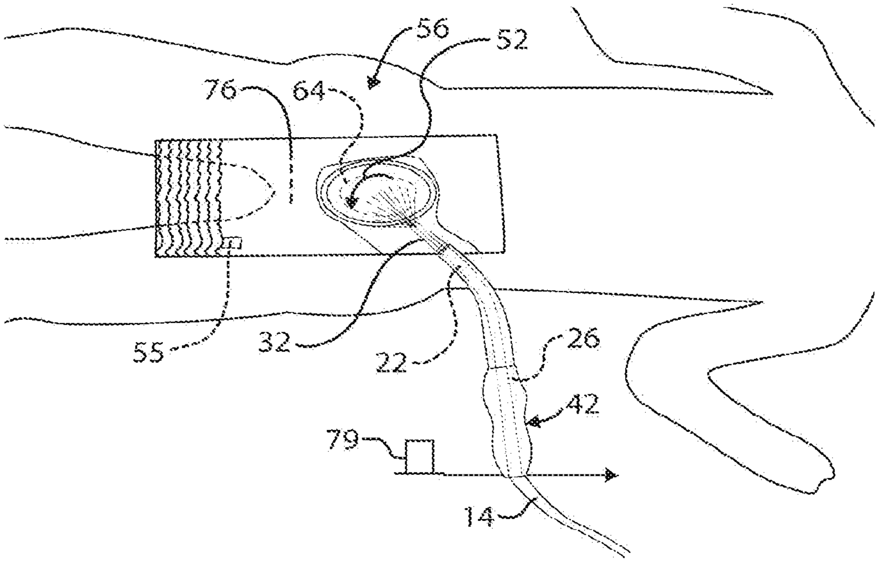
FIG. 12 is a top plan view of FIG. 11, partially cut-away, showing the distinctive irrigation spray of the inventive device, assembly and system, to debride the wound tissue and disrupt biofilm which is carried away with the effluent from the wound site for collection within the bag by the flocculent material that solidifies the effluent into a gelatinous state to be compactly disposed of upon conclusion of the treatment.

According to a second aspect of the present invention, a wound irrigation assembly 54 is described. Included is device 10 with tube 14 having inlet 16 for connection with reservoir 20 of irrigation solution 18 and an outlet via distal tip 22. Hand piece 42 captures barrel 28. Nozzle 24 is aligned with inner diameter 48 of tube outlet 22 and is captured by hand piece 42, preventing relative motion therebetween. Also included in assembly 54 is a clear plastic containment and collection bag shown with two variations, i.e., a torso wound version 56 and an extremity wound version 58. Bags 56, 58 are made of a generally tubular sheet stock unrolled (Arrow 63) from a spool 65 (FIGS. 3A-B) that includes a lower patient-side layer 60 and an upper device receiving layer 62. Patient-side layer 60 has a fenestration 64 sized to accommodate wound 12 and a dual sided adhesive tape 66 with one side 68 adhered on the patient side layer along an outer border of the fenestration. Tape 66 forms a polygonal (FIG. 1) or rounded (FIG. 2) lateral flow barrier 70 when an opposite side 72 of the tape is adhered to a patient's body 74 in alignment with wound 12. Upper side 62 of bags 56, 58 allows for a random access point chosen by the user to be snipped in a bag with scissors 74 through which nozzle 24 passes thereby transporting sterile solution 18 into a sterile operating field 76 delimited within the given bag. In FIG. 9, an ovoid tape dam 66 is shown with extremity bag 58 having an open end 59 for insertion of the bodily extremity as shown in FIGS. 5-8. The open end 59 is provided with double-sided tape 67 and may also be provided with elasticized gathers made of hook and loop material (Velcro®) as shown in FIGS. 4-8. Nozzle 24 has body 32 formed with a distally leading channel 34 presenting a semispherical first spatial conformation 38 and a proximally leading opening 36 formed in the body presenting a second spatial conformation 40 intersecting the semispherical terminus. This relationship defines an effective diameter of nozzle 24 that determines a corresponding spray pattern onto wound 12.

The peristaltic pump 77 in the present irrigation system has a key feature, which is the spray pattern created by the tip of the spray nozzle 24, shown by the several illustrated embodiments of the invention. This system utilizes a direct continuous flow of irrigating fluid that is directed under low pressure (less than 15 PSI) to the surface of wound 12 for debridement and removal of detritus. The pump 79 is used in conjunction with a tube set including an inlet portion 87 and an outlet portion 16. This differs from the pulsatile irrigator system discussed previously, i.e., where a mini-piston pump creates a power stroke accelerating the flow to a peak pressure of fluid flow achieving the same pressure level (less than 15 PSI). The principle characteristic of the pulsatile pump flow is the 'splash' effect created when the fluid is expelled from the tip (not shown). Altering the tip dimension may change the pulsatile flow, but the explosive discharge at peak pressure creates an aerosolized spray that entrains disrupted biofilm where it presents a health hazard to caregivers and patients.

An important determination of the peristaltic irrigation result is exactly what the nozzle spray looks like. Options may include a fan shape of various angles, a cone shape, or a four-square shape. Following the diagram of a fan shaped spray nozzle in FIG. 29, there are two key elements that determine the spray flow. First is the semispherical hole 34 that extends from the inlet 35 to the nozzle tip. The distance of the dome 38 of the hemisphere to the tip surface can influence the fan spray by determining the width of the spray pattern. The closer the dome 38 is to the surface, the wider the "V" notch 40 may be, and this allows for a wider spray pattern. As the dome 38 moves away from the tip, the "V" notch narrows, (not shown) which will narrow the spray pattern. Although not shown, similar effects can occur with a cone spray, where a cone is drilled from the tip down to the semisphere. The "V" notch can be made as an axial plane cut in the distal tip surface that exactly centers on the semisphere surface (not shown). The limbs of the "V" cut can be wider or narrower. To create a 'four square' spray pattern, a second "V" shaped cut can be made that centers on the semisphere and is perpendicular to the first cut (not shown). One may consult the well-known Bete Catalog, at Page 57, standard flat spray nozzle; NF10—⅛" NPT; 15 PSI; Max Flow 0.61 GPM; Equivalent Tip Orifice Diameter—0.080" Spray Angles 30°, 65°; Available Materials are brass, 303 Stainless Steel, 316 Stainless steel, and PVC (plastic).

The other important consideration is the flow rate of the peristaltic pump 77 that approximates the maximum pressure allowed (15 PSI) when the RPM of the pump reaches the maximum. As the subtle differences in the creation of the nozzle spray 52 are unique to the material machining or molding process, the surface area of the hole 38 in the nozzle tip 24 determines the pressure at a given rate of flow. Therefore, the system design must work backward from the chosen pressure limit, the maximum flow rate determined by the peristaltic pump 77 at a given RPM, and the final tip area.

Figure 13:
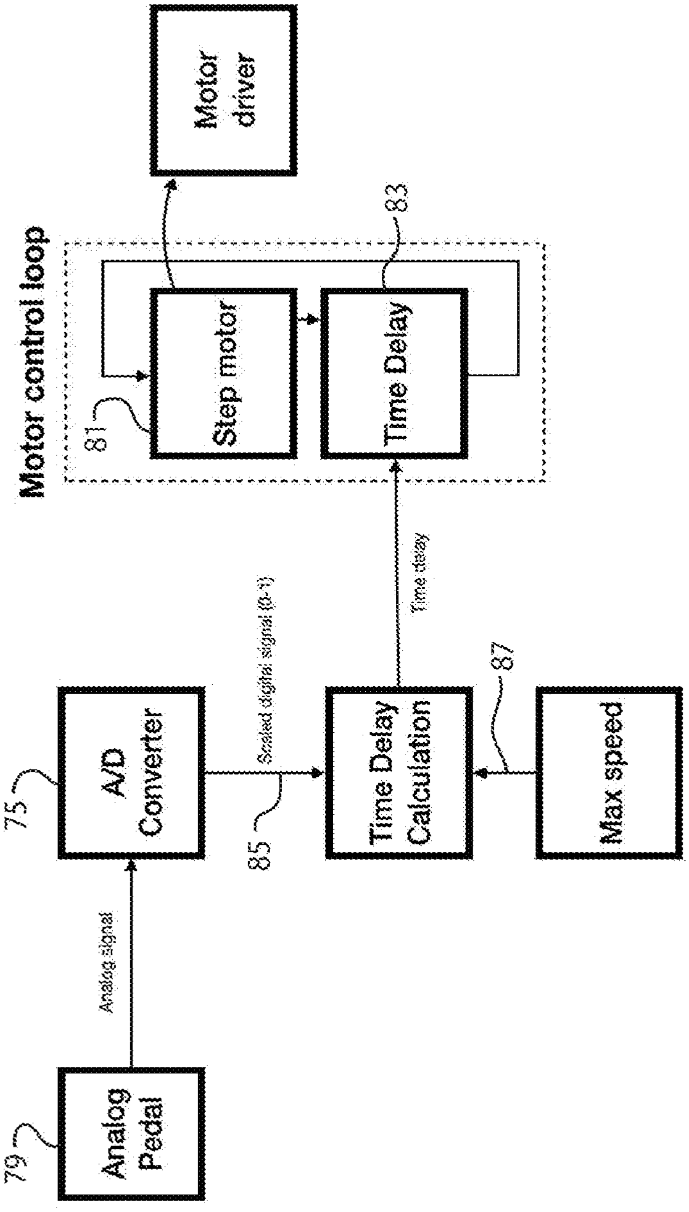
FIG. 13 is a schematic diagram of optional controls for a preferred pedal operating the peristaltic pump of the present system, that is, a variable foot pedal that would either create an analog or digital signal to increase or decrease the peristaltic pump speed (RPM)

In FIG. 13, there is disclosed a system for creating a digital signal to regulate the speed of a peristaltic pump operated by a foot pedal 79. The system includes the step of counting ticks in an encoder using an optical or electrical signal and the step of inputting the signal to the system. A further step is converting the signal input to a digital scale from 0 to 1, either through an analog to digital convener 75 or a counting microprocessor. A stepper motor 81 is provided and the digital scale is used to alter the time step between cycles of the stepper motor. Phases of the stepper motor 81 are alternated. The lag between each charge of the phase by the digital signal is modulated. The time delay 83 is changed by dividing the minimum delay over the scaled input signal 85 for a Minimum Delay/Input Signal. As the input signal is reduced from 1 to 0, the motor reduces speed 87.

Figure 14A:
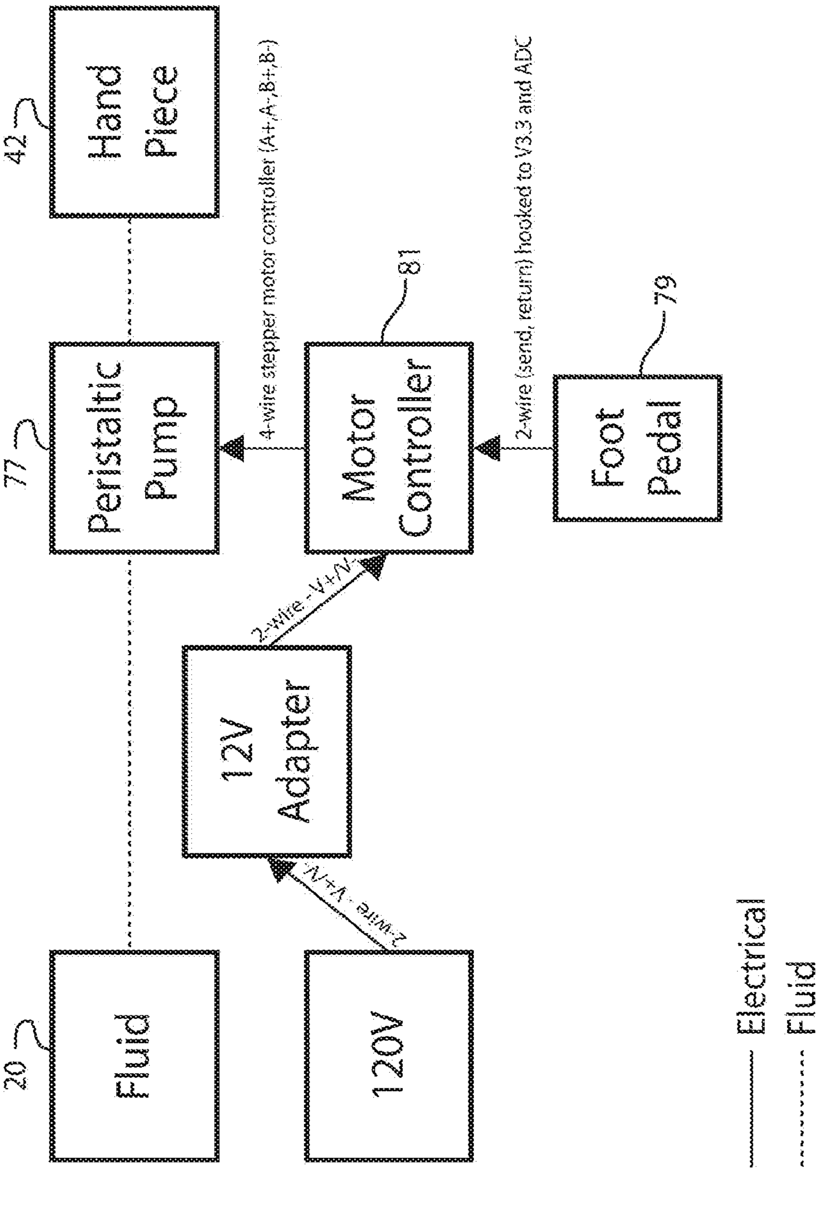
FIG. 14A is a schematic diagram that further elucidates one optional analog pedal control set-up where the change in resistance rotates or translates a potentiometer to affect the pump speed.

FIG. 14A shows a basic wiring diagram for the various electrically controlled components of the foot pedal 79 control systems, which the reader should find self-explanatory from the descriptive labels accompanying the component setup.

Figure 14B:
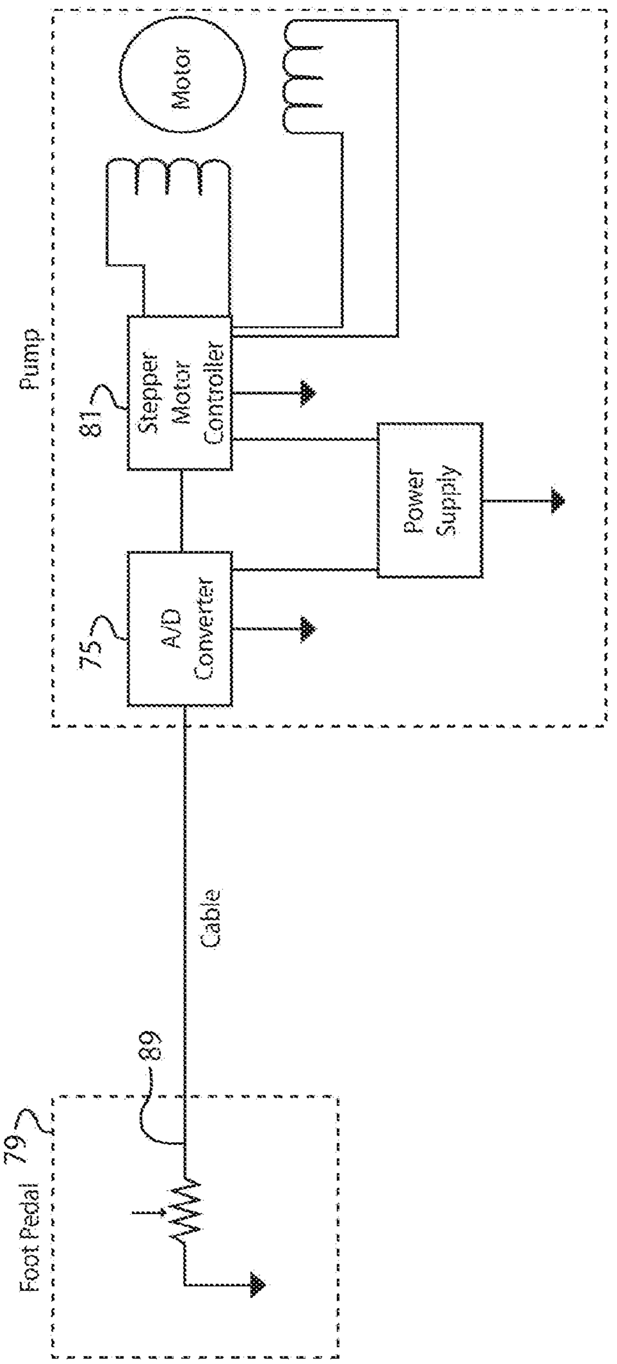
FIG. 14B is a schematic diagram that further elucidates another optional control set-up that creates a digital signal by counting ticks in an encoder using an optical or electrical signal, the signal then input to the system and converted to a digital scale from 0 to 1 either through an analog to digital converter or a counting microprocessor, the digital scale used to alter the time step between cycles of a stepper motor, so as the stepper motor alternates phases, the lag between each charge of the phase is modulated by the digital signal, the time delay being changed by dividing the minimum delay over the scaled input signal (Minimum Delay/input Signal), then as the input signal is reduced from 1 to 0, the motor reduces speed.
Figure 15:
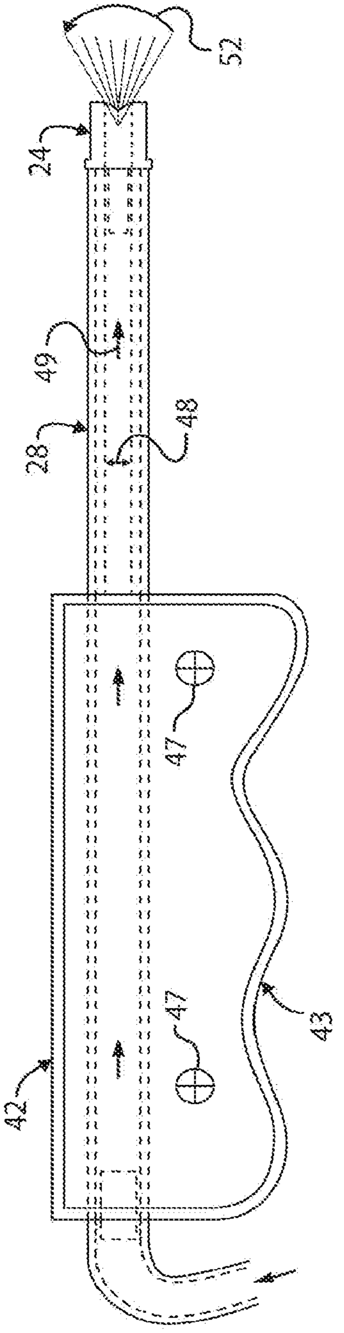
FIG. 15 is a side elevational view of an alternative preferred irrigation device of the present invention, indicating the flow of irrigation solution through the tube of the device which is surrounded by an alternative handle grip, the solution exiting through a preferred nozzle of the invention, imparting a distinctive flat spray pattern that irrigates the wound.
Figure 17B:
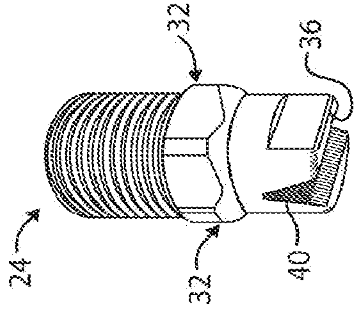
FIG. 17B is a perspective view of the nozzle of FIG. 17A, rotated somewhat less than 90 degrees, according to the present invention.
Figure 17A:
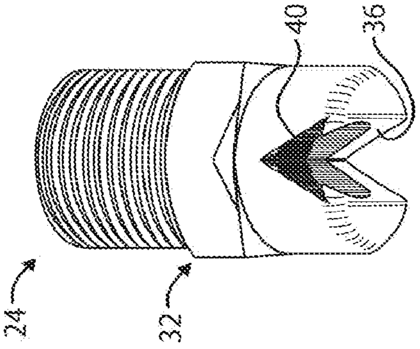
FIG. 17A is an enlarged perspective view of an alternative threaded nozzle of the present invention, indicating a V-notch further illustrated in FIG. 29.
Figure 16:
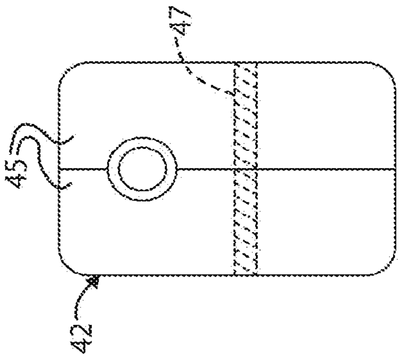
FIG. 16 is an end elevational view of FIG. 15, showing the preferred molded construction of its handle according to the present invention.
Figure 21:
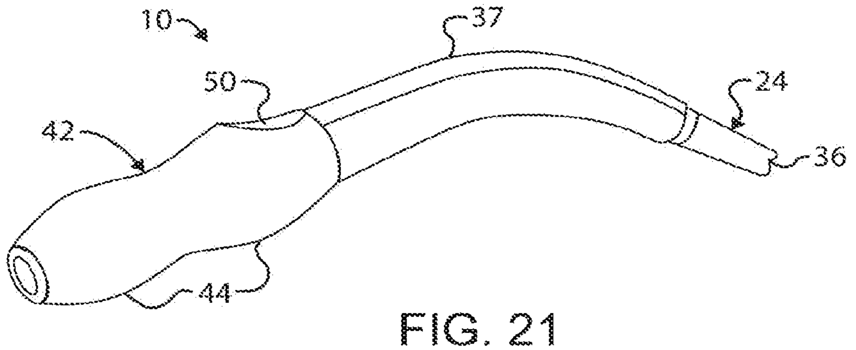
FIG. 21 is an external perspective view of a preferred device with bulbous shape of the present invention.
Figure 22:
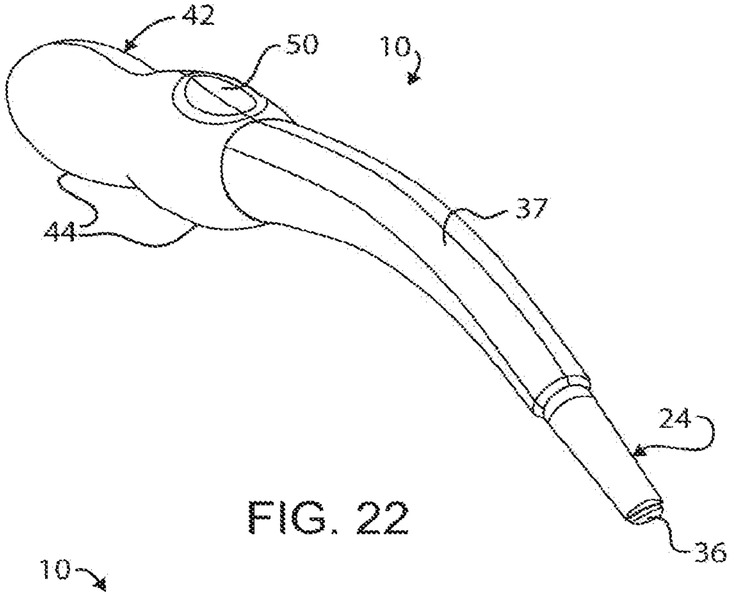
FIG. 22 is a different external perspective view of the device of FIG. 22.
Figure 23:
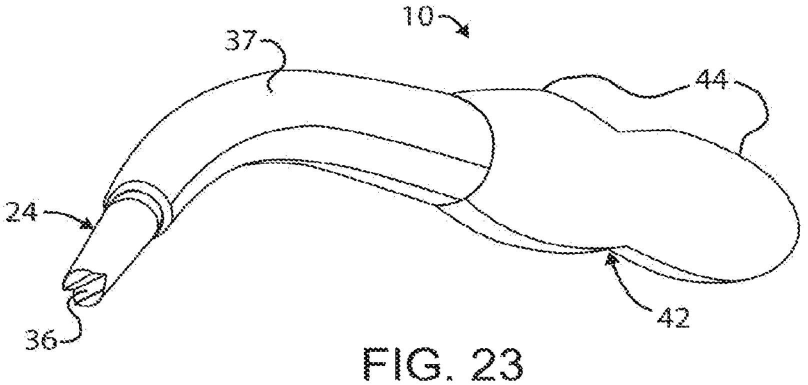
FIG. 23 is yet a different external perspective view of the device of FIG. 22.
Figure 24:
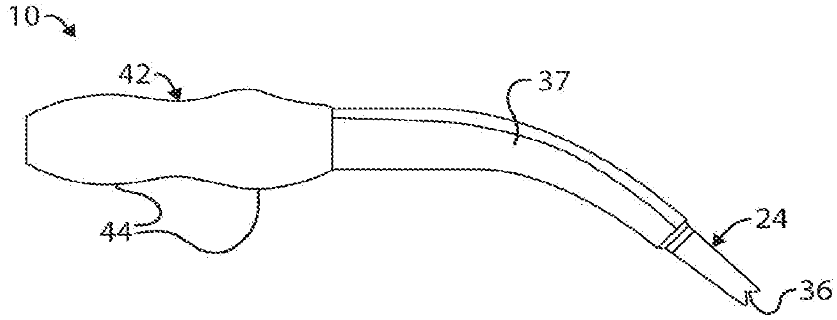
FIG. 24 is a side elevational view of the device of FIG. 22.
Figure 25:
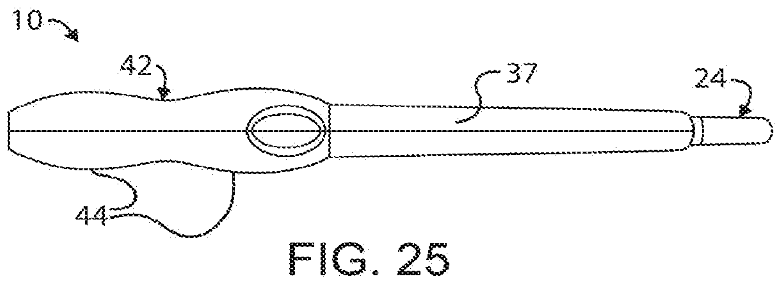
FIG. 25 is a top view of the device of FIG. 22.
Figure 26:
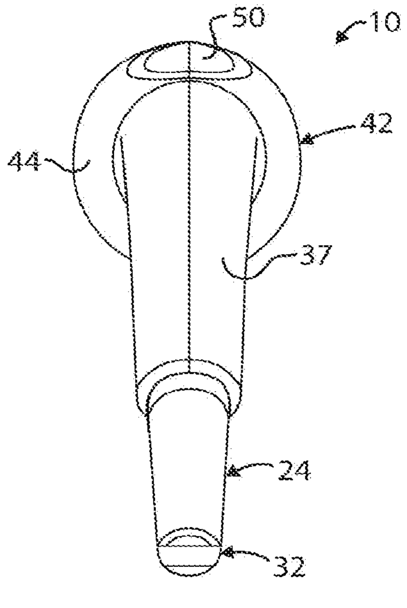
FIG. 26 is a front elevational view of the device of FIG. 22.

FIG. 14B shows one optional analog pedal 79 control set-up where the change in resistance 89 rotates or translates a potentiometer to affect the pump speed.

The bags 56, 58 of assembly 54 preferably contain a biocidal flocculent material 55 that solidifies effluent 71 within the bag 56, 58 for easier collection and disposal. Bags 56, 58 of assembly 54 preferably define a rectangular shape, being sealed at the longitudinal creases 57 on the opposed longitudinal sides (i.e., in the spooling direction) and cut and impact-sealed (Arrow 61) at the ends 69 of the bag blank. This configuration ideally accommodates a torso wound irrigation procedure, the fenestration 64 being formed intermediate the longitudinal creases 57 and ends (hatched lines) of the bag 56 to be adhered by the tape dam 66 to the patient's body 74. Alternatively, the bag 58 is cut and sealed (by action of lever as shown) on only one of the ends opposite the open end 59 so that three sides of the rectangular bag blank are closed. There is thus an opening 59 at the one end to allow ingress of an upper or lower bodily extremity 74 for irrigation of a wound 12 thereon. The open side 59 is secured by tape and/or gathers 67 around the extremity 74 to prevent disengagement of the bag 56 prior to completion of the procedure. The tape dam 66 constrains lateral flow of effluent 71 within the bag for collection and disposal, similar to the design of torso bag 56. The nozzle 24 of assembly 54 has an alternately preferred proximally leading generally wedge shaped formation 36 in the body 32 and presents an apical spatial portion that intersects with the semispherical terminus 38 of channel 34 to determine the spray pattern 52. Alternatively, though not specifically shown in the Figures, the assembly nozzle may have a proximally leading generally conically shaped formation in the body, the cone presenting an apical spatial conformation that intersects with the semispherical terminus of the channel. The assembly nozzle preferably has an effective diameter that determines a generally flat spray pattern 52 coinciding with a profile of the wound 12.

According to a third aspect of the present invention, a system for debridement and irrigation of an outpatient wound 12 will now be described. Device 10 includes tube 14 having inlet 16 and outlet tip 24 with barrel 28 therebetween and an elongated hand piece 42 with lobes 44 mounted in fixed position around the barrel. Nozzle 24 is mounted at a distal portion 26 of tube 14 and hand piece 42 without relative motion between the nozzle, tube and hand piece, respectively. A generally rectangular clear plastic tubular containment and collection bag having at least three (58) and up to all four (56) sides of the bag periphery is sealed as described above relative to assembly 54. Fenestration 64 is formed in the lower patient side 62 of the bag bordered by a dual-sided tape dam 66 which, when adhered also to the patient 74, confines lateral flow of effluent 71 to the space within the bag for collection of the effluent and disposal of the bag. The fenestration 64 and corresponding tape dam 66 profiles are selected from generally rounded or polygonal shapes (FIGS. 1-2), depending upon a given wound site 12.

Figure 27:
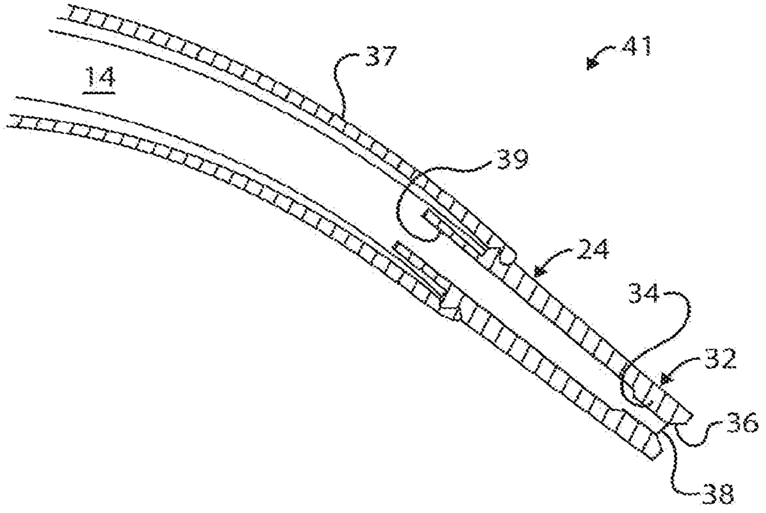
FIG. 27 is a partial sectional view of the barrel of the device of FIG. 24, enlarged from FIG. 28 (circled portion)
Figure 28:
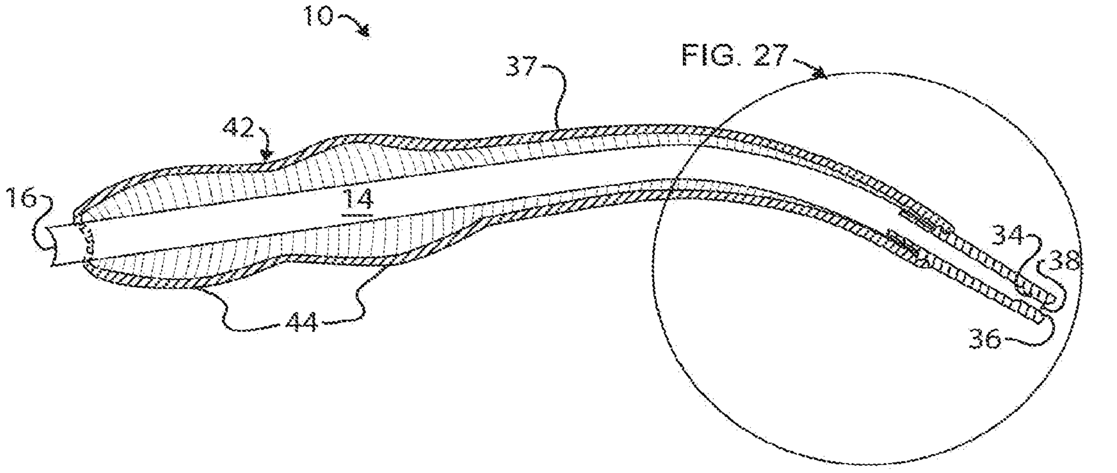
FIG. 28 is a full sectional view of the device of FIG. 24 showing the tube captured by the hand piece of the invention.
Figure 29:
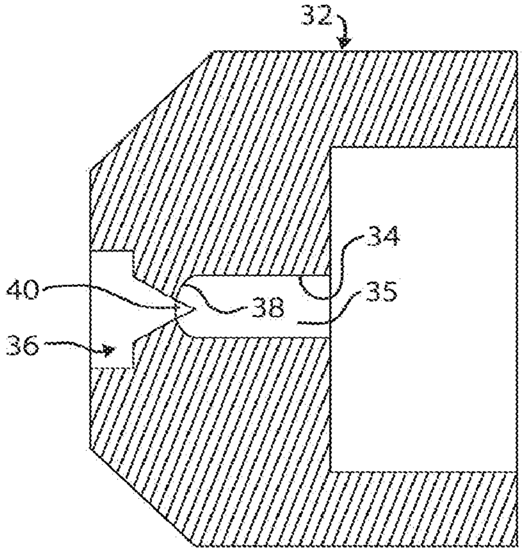
FIG. 29 is a sectional view of a plug for an outer trim fixture, according to the present invention.
Figure 30:
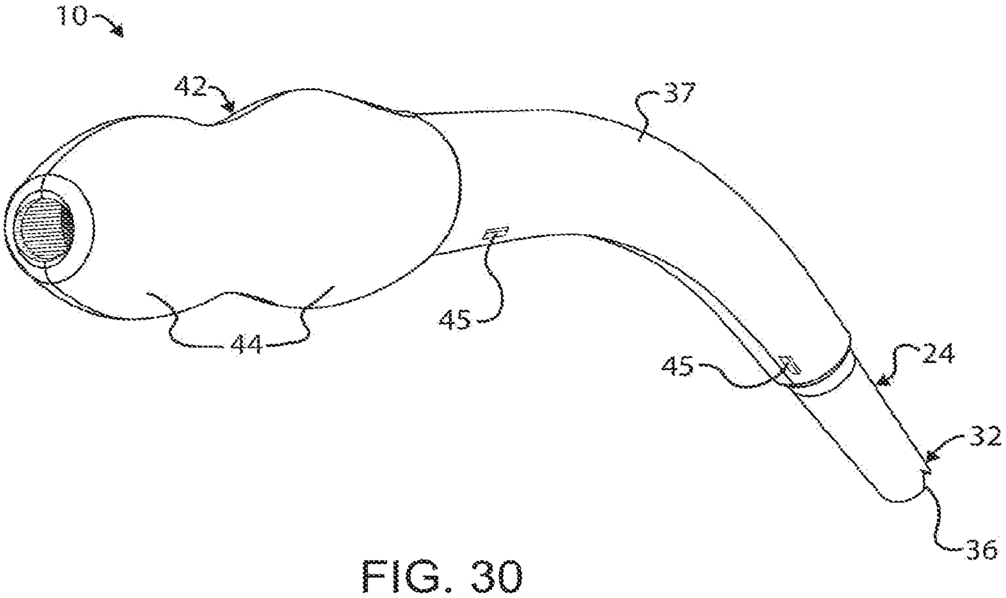
FIG. 30 is a rear external perspective view similar to FIG. 21, showing preferred locking tangs for securely snapping the molded halves of the device.
Figure 31A:
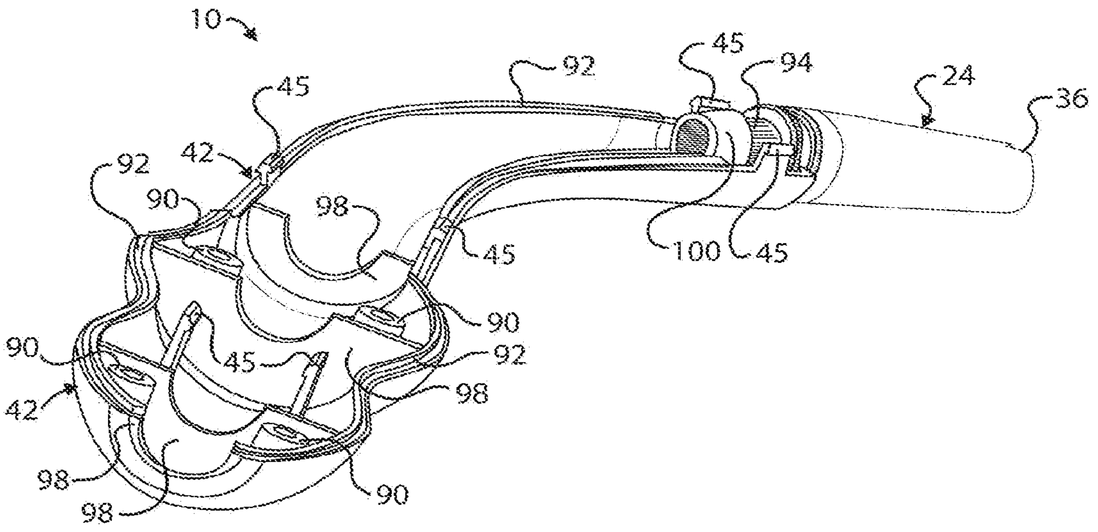
FIGS. 31A-B are matching internal perspective views, partially cut-away at the nozzle juncture, showing the corresponding snap-together elements of the device halves for capturing the tube of the present invention.
Figure 31B:
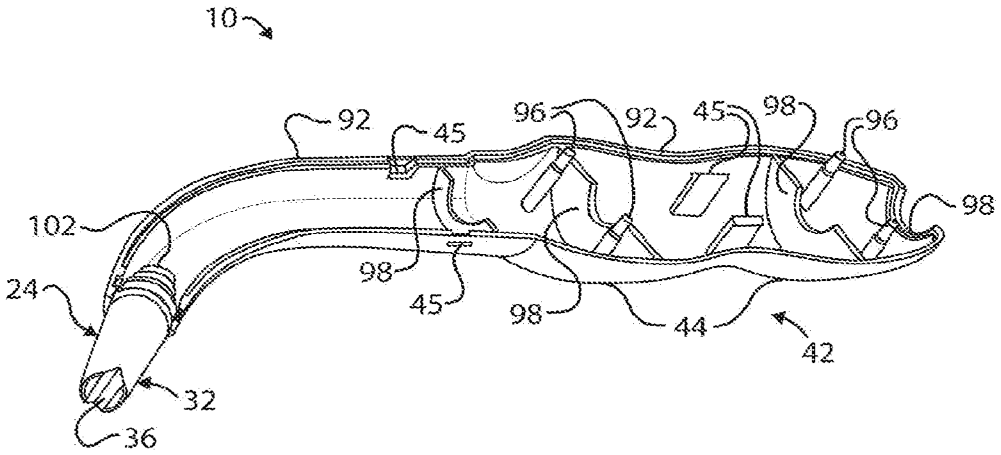
Figure 32:
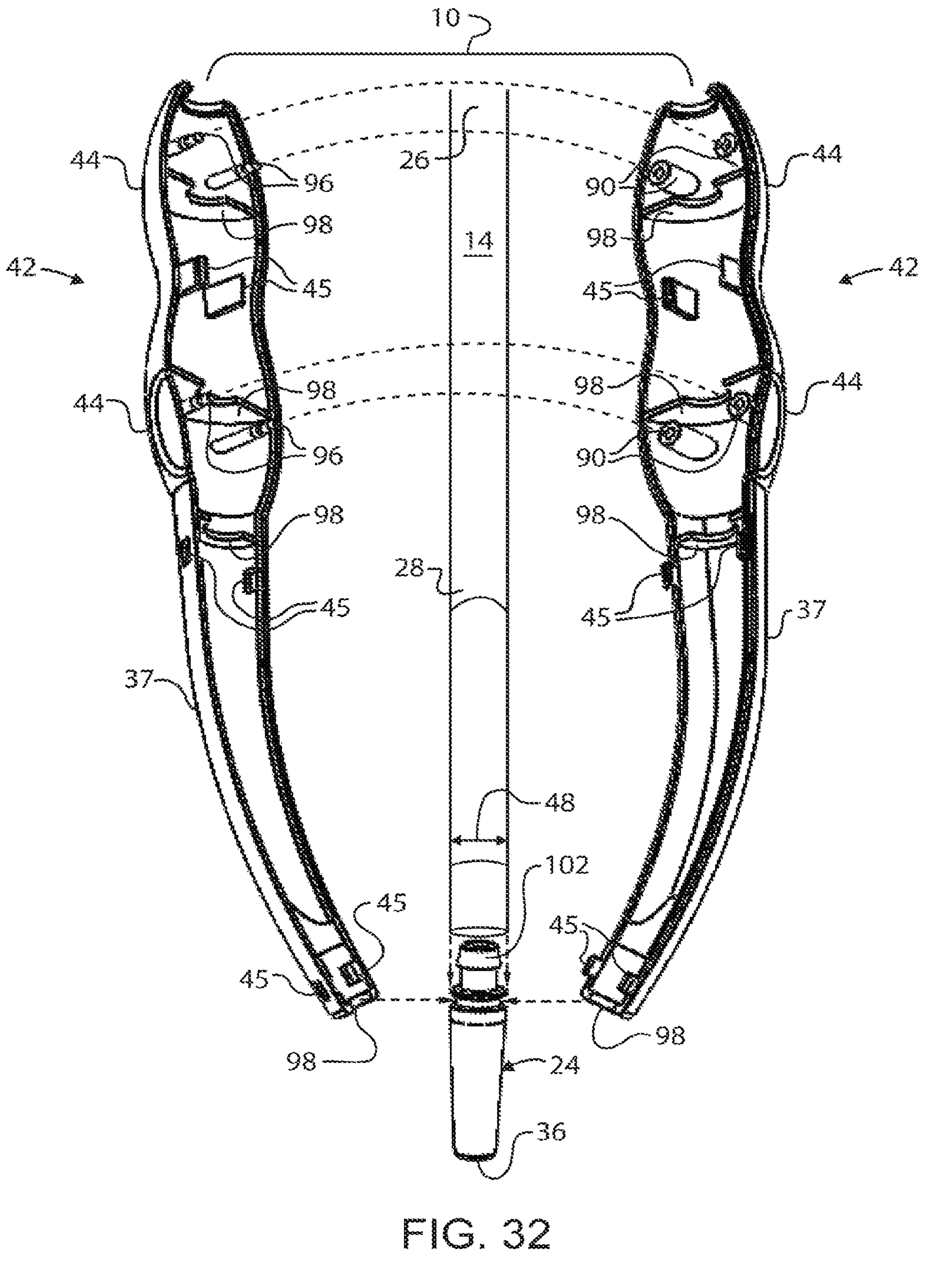
FIG. 32 is an exploded perspective view showing the mating elements of the internal halves of the device (dotted lines), particularly showing the tube with respect to the nozzle showing a securement barb of the nozzle, according to the present invention.

Referring to FIGS. 21-32, there is further shown a device 10 with delivery tube 14 enclosed tightly by preferred plastic hand piece 42 with bulbous grip 44 of the present invention. Various cooperating fastening members will now be described that are molded within the hand piece for snapping the mating halves thereof together to securely capture tube 14 against relative motion with hand piece 42. Particularly, FIGS. 21-26 are a series of orthogonal external views of the device 10, illustrating the ergonomic hand piece 42. Common structures are indicated by nozzle 24 and V-notch 36, vent hole 50, and an elongated downwardly tapering neck 37. FIG. 27 shows a barb 39 of the proximal nozzle interlocking with distal end 41 of neck 37. FIG. 28 shows the fully captured length of tube 14 with internal diameter aligned with the bore of nozzle leading into channel 34 with semispherical terminus 38 spaced from V-notch 36, as hereinbefore described. The adjoining structures of hand piece 42 are shown relative to passage of tube 14. FIG. 30 shows the mating halves of preferred bulbous hand piece 42 snapped together via locking tangs 45, also showing visible mold part lines leading from neck 37 to nozzle 24. FIGS. 31A and 31B are cut away to further reveal locking tangs 45, tube 14 retaining ribs 98 and seats 90 to receive pegs 96 from FIG. 31B and mating peripheral alignment grooves 92 on both molded halves. A serrated groove 94 on proximal barb 100 is seated at 102 in FIG. 31A. FIG. 32 shows in exploded form the mating halves of the hand piece 42 of device 10. The internal snap-in structures are shown in corresponding relationship to one another on the opposed molded halves, as detailed above in connection with FIGS. 31A and 31B.

The system preferably includes a sterile packet with a disposable wipe (not shown) containing an antiseptic such as Chlorhexidine Gluconate ("CHG") or the like in terms of safety and efficacy. Another alternative antiseptic is Hypochlorous Acid that has shown effective bacterial biofilm control, however, the regulatory approval of the antiseptic remains in progress relative to wound irrigation. Hypochlorous Acid, in an optical dosage form, is currently available in OTC products.

Importantly, the device, assembly and system aspects of the present invention, described above, utilize a peristaltic pump 77 fitted with a tube set (16, 87) which is supplied with irrigation solution 18 from a reservoir 20. To calculate pump pressure in a peristaltic pump system, one needs to know the basic flow velocity and the inner diameter of the pump tubing. Using Bernoulli's formula, the pressure of the system can be determined for comparison:

$$P = \frac{1}{2}\rho v_2$$

Bernoulli formula with ρ as the constant of 1000 kg/m$^3$ $\dot{V}$=v·A Volumetric flow rate from flow velocity times area of tube inner diameter $$A = \pi D^2 \frac{1}{4}$$

Area of tube inner diameter $$P = \frac{pV^2}{2A^2}$$

Substitution of Volumetric flow $$P = \frac{8pV^2}{\pi D^4}$$

Substitution of Area

The pump delivers a flow rate between about 800 milliliters per minute to about 2550 milliliters per minute at a constant pressure of 15 PSI, wherein the effective diameter of the nozzle 24 is between about 1.1 millimeters and 1.93 millimeters, and further wherein an effective diameter of 2.14 millimeters creates a distal tip flow pressure of 10 PSI for an optimal flow rate of 2550 milliliters per minute. This results in a three liter reservoir 20 of irrigation solution 18 being drained in merely a few minutes. To calculate the optimal distal tubing 14 inner diameter that would render 15 PSI of fluid pressure with the above peristaltic pump that has a maximum setting of 300 RPM's with a flow rate measured at 2550 milliliters per minute one may use the following formula.

$$P = \frac{8pV^2}{\pi^2 D^4}$$

Where $\dot{V}$=2550 ml/min=0.0000425 m$^3$/sec $$P = \frac{8(1000\ \text{kg/m}^3)\cdot(.0000425\ m^3)^2}{\pi^2 D^4}$$

P for 15 PSI=103,421 kg/meter sec$^2$ (Pascals)

D$^4$=(0.00001445)$^{m3}$/(1020724/m)

$$D = \sqrt[4]{.00000000014157} = 1.93\ \text{mm or } 0.076\ \text{inches}$$

The other factor to be weighed is the splatter effect magnified by the pulsatile flow of prior devices of this type. Again, the pressure of the piston pump is constant causing the same splatter effect even at lower RPMs. The uneven flow effect is minimally seen in the peristaltic pumps at rather low RPM and disappears at higher RPM. As fluid is incompressible, the pressure drops very slightly with the wave drawing fluid behind the fluid roller. This allows for a steady continuous stream flow of fluid from the distal tip of the device which some believe is more effective at removing biomass compared to a pulsed stream.

The advantages for the peristaltic pump 77 include the fact that the pump becomes a durable item that may be reused many times with standard maintenance. This will lower the costs. The piston pump loses sterility and must be disposed of after a single use because of potential biomass contamination. The operator has control of the pressure with the peristaltic pump 77 being gentler at lower RPM and more brisk and stiff at higher RPM of the pump. This can be done with a manual dial or an electrically activated variable output foot pedal 79 that controls the RPM, as discussed relative to FIGS. 13 and 14A-14B above.

Peristaltic pumps made by Prefluid Ltd of Changzhou, China have been found acceptable herein, particularly Model MP 300-TH162 having a flow rate range from 0.001-2700 mi/min. Specifications for the MP 300 line of pumps were accessed on Nov. 10, 2017 at www.prefluid.net/medical-peristaltic-pump/MP300-peristaltic-pump.shtml. Likewise, the Prefluid MP 200 line of peristaltic pumps was also found acceptable for certain uses. The flow rate of these MP 200-pumps is in the range of 001-560 ml/min and detailed specifications for this pump line were accessed on Nov. 10, 2017 at www.prefluid.net/medical-peristaltic-pump/MP200-peristaltic-pump.shtml. These MP 200 and MP 300 pumps are said by the manufacturer to be applicable to hospital surgical debridement.

The peristaltic pump 77 in the present irrigation system 54 has several key features that have the following characteristics. Pump 77 has a variable flow rate determined by the operator which allows for the administration of different irrigation effluents. Normal saline or water may be irrigated at the maximum pressure allowed by the maximal flow, but antiseptic solutions such as 0.05% chlorhexidine gluconate (Irrisept®) in irrigation should be applied at very low pressures that allow the irrigation solution 18 to pool in the wound 12. A unique feature of the pump system 77 is to have two separate irrigation fluids 18, 17 attached to the proximal tube irrigation channel that may be administered a different desired pressures, but still a part of the same assembly (FIGS. 5-8, 11, 12) showing two bags 19, 20 that have different fluids 18, 17. Another key feature is the spray pattern created by the tip of the spray nozzle 32 shown by several illustrated embodiments of the invention (FIGS. 5-8, 11, 12, 18). This system utilizes a direct continuous flow of irrigating fluid that is directed under low pressure (less than 15 PSI) to the surface of the wound 12 for debridement and removal of detritus. Empirical considerations suggest that the direct continuous flow with the fluid directed at an angle to the surface may be more effective than a flow directed perpendicular to the surface. The pump 77 is used in conjunction with a tube set 16, 23A-C including an inlet portion 23A and an outlet portion 16.

The foregoing description and accompanying drawings illustrate the principles, preferred embodiments and modes of operation of the invention. These should be regarded as illustrative rather than restrictive. However, the invention should not be construed as being limited to the particular embodiments discussed above. Additional variations of the embodiments will be appreciated by those skilled in the art without departing from the scope of the invention as defined by the following claims.

The invention claimed is:

1. A medical device for irrigation of a wound site, comprising:

a wound irrigation device, comprising:

a tube comprising a proximal portion including an inlet configured to receive an irrigation solution, a distal portion, and an intermediate portion configured to direct the irrigation solution between the proximal portion and the distal portion;

a nozzle positioned at the distal portion and configured to provide the irrigation solution to the wound site; and a hand piece coupled to the tube and configured to prevent rotation of the hand piece relative to the tube; and a peristaltic pump coupled to a source of the irrigation solution and configured to deliver the irrigation solution to the inlet at a flow rate between about 800 milliliters per minute to about 2550 milliliters per minute;

a containment and collection bag sized to accommodate the wound site and comprising an access point through which the nozzle passes into an interior of the containment and collection bag, wherein the containment and collection bag comprises a biocidal flocculent material configured to solidify effluent within the bag for collection and disposal.

2. The medical device of claim 1, wherein the nozzle comprises a body having a first spatial conformation intersecting a second spatial conformation to define an effective diameter of the nozzle.

3. The medical device of claim 2, wherein the nozzle comprises an opening having a geometry selected from a wedge, a cone, a tetrahedron or a star shape formation in the body.

4. The medical device of claim 1, wherein the nozzle is in a fixed position on a distal tip of the tube.

5. The medical device of claim 1, wherein the tube comprises a barrel portion, and wherein the hand piece is affixed to the barrel portion of the tube.

6. The medical device of claim 5, wherein the hand piece is formed with an integral hand grip affixed to the barrel portion of the tube.

7. The medical device of claim 1, wherein the hand piece is plastic and elongated with a bulbous shape, capturing the tube and the nozzle at a distal tip of the tube.

8. The medical device of claim 1, wherein the hand piece captures the nozzle at a distal tip of the tube.

9. The medical device of claim 8, wherein the nozzle is made of plastic and bonded to the distal tip and the hand piece by an adhesive or sonic welding.

10. The medical device of claim 1, wherein the nozzle is metallic and mechanically fastened to the hand piece at a distal tip of the tube by a threaded or crimped connection.

11. The medical device of claim 1, wherein the nozzle has a proximally leading generally wedge shaped formation in a body of the nozzle.

12. A wound irrigation assembly comprising:

a wound irrigation device, comprising:

a tube with a proximal inlet for connection with a source of irrigation solution and a distal tip with an outlet;

a hand piece capturing a portion of the tube; and a nozzle provided at the outlet; and a containment and collection bag comprising a lower patient-side layer and an upper device receiving layer, the lower patient-side layer having a fenestration sized to accommodate a wound, the upper device receiving layer configured to provide an access point through which the nozzle passes into an interior of the containment and collection bag, wherein the containment and collection bag comprises a biocidal flocculent material configured to solidify effluent within the bag for collection and disposal.

13. The wound irrigation assembly of claim 12, wherein the containment and collection bag defines a rectangular shape and the fenestration is formed intermediate longitudinal sides of the containment and collection bag.

14. The wound irrigation assembly of claim 12, wherein the containment and collection bag comprises an opening configured to receive an upper or lower bodily extremity for irrigation of the wound thereon.

15. The wound irrigation assembly of claim 12, further comprising a peristaltic pump configured to connect to the source of irrigation solution and to the proximal inlet of the tube, the peristaltic pump delivering a flow rate between about 800 milliliters per minute to about 2550 milliliters per minute.

16. A system for irrigation of a wound comprising:
a device comprising:
a tube having an inlet and outlet;
an elongated hand piece mounted in fixed position between the inlet and the outlet; and
a nozzle mounted at a distal portion of the tube;
a containment and collection bag comprising a fenestration in a lower patient side, the containment and collection bag further comprising a biocidal flocculent material configured to solidify effluent within the bag for collection and disposal; and
a peristaltic pump configured for connection to a source of irrigation solution and to the inlet of the tube.

17. The system of claim 16, further comprising a sterile packet with a disposable wipe containing an antiseptic.

18. The system of claim 16, wherein the fenestration has a peripheral shape that is generally round or polygonal in shape.

19. The system of claim 16, wherein the containment and collection bag comprises an opening configured to receive an upper or lower bodily extremity for irrigation of a wound thereon.

* * * * *